(12) United States Patent
Chen et al.

(10) Patent No.: US 7,352,179 B2
(45) Date of Patent: Apr. 1, 2008

(54) METHODS AND APPARATUS FOR MEASURING CAPILLARY PRESSURE IN A SAMPLE

(75) Inventors: Quan Chen, Fredericton (CA); Bruce Balcom, Fredericton (CA)

(73) Assignee: Green Imaging Technologies Inc., Fredericton (CA)

( * ) Notice: Subject to any disclaimer, the term of this patent is extended or adjusted under 35 U.S.C. 154(b) by 0 days.

(21) Appl. No.: 11/262,658

(22) Filed: Oct. 31, 2005

(65) Prior Publication Data

US 2006/0116828 A1   Jun. 1, 2006

Related U.S. Application Data

(60) Provisional application No. 60/622,784, filed on Oct. 29, 2004.

(51) Int. Cl.
*G01V 3/00* (2006.01)

(52) U.S. Cl. .................................................. 324/303

(58) Field of Classification Search ......... 324/300–322
See application file for complete search history.

(56) References Cited

U.S. PATENT DOCUMENTS

| | | | |
|---|---|---|---|
| 4,868,500 A | | 9/1989 | Baldwin et al. |
| 5,754,048 A | * | 5/1998 | Bielecki ..................... 324/321 |
| 5,760,586 A | * | 6/1998 | Foerster et al. ............. 324/321 |
| 5,774,960 A | | 7/1998 | De Fraguier et al. |
| 5,959,454 A | | 9/1999 | Westphal et al. |
| 6,178,807 B1 | | 1/2001 | Baldwin et al. |
| 6,255,819 B1 | | 7/2001 | Day et al. |
| 6,278,351 B1 | | 8/2001 | Wheately |
| 6,337,568 B1 | | 1/2002 | Tutunji et al. |
| 6,415,649 B1 | | 7/2002 | Spinler et al. |
| 6,489,872 B1 | | 12/2002 | Fukushima et al. |
| 6,534,984 B2 | | 3/2003 | Westphal |
| 6,583,622 B1 | * | 6/2003 | Hills ........................... 324/307 |

OTHER PUBLICATIONS

European Search Report Issued on Application No. 05256726, dated Mar. 30, 2006.
Ayappa K.G. et al., Capillary Pressure: Centrifuge Method Revisited, AIChE Journal Mar. 1989, vol. 35, No. 3, pp. 365-372, Minneapolis, MN, USA.
Quan Chen, et al, A Magnetic Resonance Study of Pore Filling Processes During Spontaneous Imbibition in Berea Sandstone, Journal of Chemical Physics, Nov. 8, 2003, vol. 119, No. 18, pp. 9609-9616.

(Continued)

*Primary Examiner*—Brij Shrivastav
*Assistant Examiner*—Dixomara Vargas
(74) *Attorney, Agent, or Firm*—Seyfarth Shaw LLP

(57) ABSTRACT

A method and apparatus are provided for measuring a parameter such as capillary pressure in porous media such as rock samples. The method comprises mounting a sample in a centrifuge such that different portions of the sample are spaced at different distances from the centrifuge axis, rotating the sample about the axis, measuring a first parameter in the different portions of the sample, and determining the value of a second parameter related to the force to which each portion is subjected due to rotation of the sample. In one embodiment, the first parameter is relative saturation of the sample as measured by MRI techniques, and the second parameter is capillary pressure.

52 Claims, 17 Drawing Sheets

OTHER PUBLICATIONS

Cunha, Christina M. C., et al., Calculating Capillary Pressure Curve from Single-Speed Centrifuge Experiments, Inverse Problems 16, Jul. 31, 2000, pp. 1897-1906, IOP Publishing Ltd., UK.

Dullien, F.A., Porous Media; Fluid Transport and Pore Structure, 1992, cover pages, 117-236, Academic Press, Inc., USA.

Purcell, W.R., Capillary Pressures—Their Measurement Using Mercury and The Calculation of Permeability Therefrom, Petroleum Transactions, AIME, Feb. 1949, pp. 39-48, USA.

Fatt, I., et al., Relative Permeability Studies, Petroleum Transactions, AIME, 1951, pp. 249-256, vol. 192, USA.

Burdine, N.T., Relative Permeability Calculations from Pore Size Distributions Data, Petroleum Transactions, AIME, 1953, pp. 71-78, vol. 198, USA.

Hassler, G.L. et al, Measurement of Capillary Pressures in Small Core Samples, Transcript AIME, Oct. 1944, pp. 114-123, USA.

Ruth, Douglas W., et al., Measurement and Interpretation of Centrifuge Capillary Pressure Curves—The SCA Survey Data, The Log Analyst, Sep./Oct. 1995, pp. 21-33, Canada.

Melrose, J.C., Interpretation of Centrifuge Capillary Pressure Data, SPWLA Twenty-Seventh Annual Logging Symposium, Jun. 1986, pp. 1-20, USA.

Rajan, R.R., Theoretically Correct Analytical Solution for Calculating Capillary Pressure-Saturation From Centrifuge Experiments, SPWLA twenty-Seventh Annual Logging Symposium, Jun. 1986, pp. 1-18, USA.

Chen, Quan, et al., Variations of Permeability and Pore Size Distribution of Porous Media with Pressure, Journal of Environmental Quality, Mar./Apr. 2002, pp. 500-505, vol. 31.

Balcom, B.J., et al., Single-Point Ramped Imaging with $T_1$ Enhancement (SPRITE), Journal of Magnetic Resonance, 1996, pp. 131-134, Series A 123, Academic Press, Inc.

Balcom, B.J. et al., Single-Point Magnetic Resonance Imaging (MRI) of Cement Based Materials, Materials and Structures, Apr. 2003, pp. 166-182, vol. 36, RILEM, Canada.

Forbes, Pierre, Centrifuge Analysis Techniques: An SCA Survey on The Calculation of Drainage Capillary Pressure Curves from Centrifuge Measurements, SCA Survey—Featured Presentation, 1997, Belgium.

Mastikhin, Igor V. et al., Sprite MRI with Prepared Magnetization and Centric k-Space Sampling, Journal of Magnetic Resonance, 1999, pp. 159-168, Academic Press, Canada.

Leverett, M.C., Capillary Behavior in Porous Solids, Transcript AIME, Oct. 1940 pp. 152-169, USA.

Forbes, Pierre, Quantitative Evaluation and Correction of Gravity Effects on Centrifuge Capillary Pressure Curves, SCA-9734, 16 pages.

* cited by examiner

| First Parameter e.g. Fluid Content | 2nd Parameter Related to Force as Function of Distance from Rotational axis |
|---|---|
| | e.g. Capillary Pressure $P_c(r)$ |
| Value 1 | Value 1 |
| Value 2 | Value 2 |
| Value 3 | Value 3 |
| Value 4 | Value 4 |
| ⋮ | ⋮ |
| Value n | Value n |

FIG. 6

METHODS AND APPARATUS FOR MEASURING CAPILLARY PRESSURE IN A SAMPLE

CROSS-REFERENCE TO RELATED APPLICATIONS

This application claims priority from U.S. Patent Application Ser. No. 60/622,784 filed on 29 Oct., 2004.

FIELD OF THE INVENTION

The present invention relates to methods and apparatus for measuring parameters in samples, and in particular, but not limited to measuring capillary pressure or other parameters in porous media, such as rock samples.

BACKGROUND OF THE INVENTION

Capillary pressure curves are widely used in material, soil and environmental sciences, and especially in the petroleum industry. Capillary pressure curves provide critical information frequently used in the assessment of the economic viability of oil reservoir development.

The two most important characteristics of a reservoir core are the porosity and permeability. These are closely followed by the in situ oil saturation, and the capillary pressure. While a slightly more esoteric quantity than the first three, the capillary pressure is fundamental to reservoir evaluation, and fundamental to many reservoir properties measured in other ways. Capillary pressure results from the pore level interaction between a wetting fluid (often water), a non-wetting fluid (often oil) and the rock matrix. Capillary processes critically affect the initial reservoir fluid distribution and petroleum recovery during primary or enhanced production. The distribution of multiple fluids in the reservoir pores are a function of capillary forces, which in turn are related to the wettability, fluid density and pore geometry, as described in F. A. L. Dullien, Porous Media: fluid transport and pore structure, New York, Academic Press, 1979.

In evaluating hydrocarbon reservoirs, laboratory capillary pressure curve measurements on extracted cores are directly applied to determine many petrophysical qualities, for example: pore size distribution, irreducible water saturation and residual oil saturation, wettability of the reservoir rock, seal capacity, depth of free water level in the reservoir, and thickness of the transition zone. The initial water and oil saturation as a function of height above the free water level, an approximation of the recovery efficiency during primary or secondary recovery, and calculation of permeability and relative permeability may also be determined by laboratory measurements of the capillary pressure, as described in the reference above and W. R. Purcell, Trans. AIME 186, 39 (1949) and I. Fat and H. Dyksta, Trans AIME 192, 41 (1951).

Capillary pressure may be obtained by either mercury intrusion, porous plate, or centrifuge methods. The mercury intrusion method is rapid, but it is destructive, and the mercury/vacuum system does not represent the wettability of reservoir system. The porous plate method is a direct and accurate technique, but is extremely time-consuming, since the equilibrium time can range from a week to months per pressure point.

The centrifugal capillary pressure curve technique was introduced by Hassler and Brunner in 1945, as described in Hassler, G. L., Brunner, E., "Measurement of Capillary Pressure in Small Core Samples", Trans. AIME, 1945, 160, 114-123 and N. T. Burdine, Trans. AIME 198, 71 (1953). This technique, which involves rotating fluid bearing rock cores at variable speeds in a specially modified centrifuge, has been extensively investigated, and is commonly used in the petroleum industry. Sample rotation yields a centrifugal force which will empty pores with matching capillary forces. Collecting the expelled fluid as a function of increasing rotational speed permits a quantification of the capillary pressure as a function of fluid content or saturation. It is however well known that many problems exist with the traditional method, ranging from fundamental concerns about the validity of the underlying theory to uncertainty over how to treat the experimental data.

The traditional interpretation of centrifugal capillary pressure data is based on several assumptions: (1) Nonlinearity of the centrifugal field is not significant; (2) Gravity has no effect on fluid distribution; and (3) The capillary pressure is zero at the bottom (outlet end-face) of the core plug. These assumptions are known to lead to significant errors in the measurement of the capillary pressure curve. In addition, these three conditions can not be simultaneously satisfied. The first assumption requires a short sample and large rotational radius. For low capillary pressures, the experiment requires a very low rotational speed. In this case, the effect of gravity can not be neglected. For high capillary pressures, the experiment requires a very high rotation speed, which is likely to lead to a violation of the third assumption (capillary pressure is zero at the outlet). In addition, the rock pore structure in unconsolidated or friable samples (for example marginal reservoirs) will change due to the high centrifugal forces, thereby altering the capillary pressure curve.

Traditional centrifuge methods for capillary pressure determination are time consuming and special instrumentation is required for the experiment. Measurement of the full capillary pressure curve requires approximately 15 different centrifuge speeds, thus requiring one day to several days for measurement. In addition, some friable and unconsolidated rock samples may be broken during ultracentrifugation, as described in D. Ruth and Z. Chen, The Log Analyst 36, 21 (1995). The experiment requires a very expensive ultracentrifuge with precise speed control over a wide range of speeds. A special core holder and stroboscope for collecting and measuring expelled liquid are also necessary for the experiment.

Magnetic Resonance Imaging (MRI) is a powerful, non-destructive, measurement method, which, with techniques developed by the inventors described in Balcom, B. J., MacGregor, R. P., Beyea, S. D., Green, D. P., Armstrong, R. L. and Bremner, T. W. "Single Point Ramped Imaging with T1 Enhancement (SPRITE)", *J. Magn. Res. A* (1996) 123, 131-134, offer unique advantages in the measurement of spatially resolved fluid saturation in porous media, discussed in Chen, Q., Gingras, M. and Balcom, B. J., "A magnetic resonance study of pore filling processes during spontaneous imbibition in Berea sandstone", J. Chem. Phys., 119, 9609-9616 (2003) and Balcom, B. J., Barrita, J. C., Choi, C., Beyea, S. D., Goodyear, D. J. and Bremner, T. W. "Single-point magnetic resonance imaging (MRI) of cement based materials", *Materials and Structures* (2003) 36, 166-182.

When two immiscible fluids (wetting phase and non-wetting phase) are in contact in the interstices of a porous medium, a discontinuity in pressure exists across the interface. The difference in pressure is called the capillary pressure, $P_c$, which is defined as the pressure in the non-wetting phase minus the pressure in the wetting phase.

$$P_c = P_{non-wetting} - P_{wetting} \quad (1)$$

The hydrostatic pressure (P) of a liquid with density $\rho$ is dependent on the elevation z as follows $$\frac{dP}{dz} = \rho g \quad (2)$$

where g is the acceleration due to gravity.

For an oil-water porous media system in a reservoir, if water is the wetting phase and oil is the non-wetting phase, the capillary pressure is related to the height of the fluid above the free water level (where water saturation is 100%, above this level, the water saturation is less than 100%) as $$\frac{dP_c}{dz} = (\rho_0 - \rho_w)g \quad (3)$$

If fluid columns are continuous in the reservoir, the following relationship holds $$P_c(z) = P_c(z_0) + g\int_{z_0}^{z}(\rho_0 - \rho_w)dz \quad (4)$$

where g is the acceleration due to gravity, $z_o$ is the free water level in the reservoir, $P_c(z)$ is the capillary pressure at height z above $z_0$, and $\rho_w$ and $\rho_o$ are the densities of water and oil, respectively.

If the water saturation at $z_0$ is 100% and, thus, $P_c(z_0)=0$. Equation (4) can be expressed as $$P_c(z) = g(\rho_0 - \rho_w)(z - z_0) \quad (5)$$

The capillary pressure is a result of the curvature of fluid interfaces, according to the well-known Young-Laplace equation $$P_c = \sigma\left(\frac{1}{R_1} + \frac{1}{R_2}\right) \quad (6)$$

where $\sigma$ is interfacial tension between the two fluids and $R_1$ and $R_2$ are principle radii of curvature.

If the pore throat shape of the rock can be described as a cylindrical capillary tube, equation (6) becomes $$P_c = 2\sigma \cos \theta / R \quad (7)$$

where R is the pore throat radius, and $\theta$ is the contact angle.

The capillary pressure can be converted directly into a pore throat size using equation (7).

Laboratory measurements of the capillary pressure curve can be converted into capillary pressure curves under reservoir conditions. The condition for capillary forces to exist is a curvature of the fluid-fluid interface. The relation between fluid saturation and capillary pressure in the reservoir is a function of the pore sizes, wettability, interfacial tension and fluid saturation history (drainage and imbibition). Based on laboratory measurements of the capillary pressure, it is possible to convert these into reservoir capillary pressure with equation (7-2).

$$\frac{P_c^R}{P_c^L} = \frac{(\sigma \cos \theta)_R}{(\sigma \cos \theta)_L} \quad (7-2)$$

Where $P_c^R$ and $P_c^L$ are the capillary pressure under reservoir and laboratory conditions, respectively; $(\sigma \cos \theta)_R$ and $(\sigma \cos \theta)_L$ are the products of interfacial tension and cosine of contact angle under reservoir and laboratory conditions, respectively.

Equation (7-2) can also be applied to convert capillary pressure curves under other, different conditions.

As described in Hassler, G. L., Brunner, E., "Measurement of Capillary Pressure in Small Core Samples", Trans. AIME, 1945, 160, 114-123, Hassler and Brunner proposed a centrifuge method to obtain capillary pressure-saturation data from small core plugs. They also proposed an approximate solution to the basic equation relating capillary pressure and average saturation by neglecting the gravity gradient across the core and assuming the length of the core was negligible compared to the radius of rotation.

The rock sample for centrifuge capillary pressure curve measurements is assumed to be homogeneous, isotropic, and rigid. The mineral grains are taken to be incompressible. Thus, the pore structure of the rock is independent of the magnitude of the capillary pressure imposed. Similarly, the density of either fluid (wetting or nonwetting, if a liquid), is assumed to be independent of capillary pressure. If the non-wetting phase is a gas, the density is assumed to be negligible.

The surface or interfacial tension between the wetting fluid and non-wetting fluid is assumed to be constant, implying isothermal conditions. The wetting characteristics of the three-phase system are considered to be independent of the magnitude of the capillary pressure. Thermodynamic equilibrium is assumed to exist throughout the sample.

A conventional centrifuge capillary pressure experiment is illustrated in FIGS. 1A and 1B. The experimental apparatus comprises a centrifuge which includes a motor 1, a driveshaft 3 having a rotational axis 5, an arm 7 extending radially from the driveshaft 5 and a sample holder 9 pivotally mounted to the end 11 of the arm 7 so that the sample holder is free to swing up and down. The sample holder includes a removable, sealed end part 13 at the inner end 15 and a porous plate core holder 17 which divides the volume of the sample holder into a first volume 19 for accommodating a reservoir rock core sample and a second volume 21 for receiving liquid expelled from the rock core.

Initially, the sample core is saturated with a fluid, for example water, and the sample holder contains another fluid, for example air, which replaces the fluid displaced from the core as the sample is spun.

As illustrated in FIGS. 1A and 1B, $r_1$ is the distance from the axis of rotation 5 to the inlet end-face 23 of the sample core, $r_2$ is the distance from the axis of rotation 5 to the outlet end-face 25 of the sample core, while r is the distance from the axis of rotation to any point along the core length.

To measure the capillary pressure curve, the relative saturation of the sample core is measured as a function of capillary pressure which varies as a function of angular velocity of the centrifuge. Thus, a series of measurements are made at different rotational speeds to provide a series of data points of relative core saturation and capillary pressure. For each measurement, the centrifuge is spun at a particular speed and fluid is expelled from the outlet end-face of the sample into the end volume 21 and at the same time replacement fluid in the sample holder is drawn into the sample core. After reaching equilibrium fluid displacement at each speed, the amount of liquid expelled from the core is measured with a stroboscope while the centrifuge is in motion, as described in Rajan, R. R., "Theoretically Correct Analytical Solution for Calculating Capillary Pressure-Saturation from Centrifuge Experiments," SPWLA 27$^{th}$ Annual Logging Symposium, Houston, Tex., Jun. 9-13, 1986. By knowing the pore volume and initial fluid saturation in the core, the average volume remaining in the core at each different speed can be calculated from observation of the liquid produced, i.e. the liquid in the end volume 21. The rotational speed of the centrifuge is increased in steps and the measurement process repeated at each different speed. Typical experimental data points are depicted in FIG. 2. A complete capillary pressure curve usually requires about 15 speeds (15 data points) and may take one to several days to acquire, and therefore obtaining a capillary pressure curve is a relatively slow process. Another drawback of this conventional method is that it requires a special centrifuge which is capable of providing a wide range of angular velocities and therefore the centrifuge is relatively expensive.

The basic concepts for capillary pressure measurement with a centrifuge are outlined below for an assumed small core rotating at high angular velocity.

If the cylindrical core of length L is subjected to an acceleration $a_c = -\omega^2 r$, where $\omega$ is the angular velocity of the centrifuge and r is the distance from the axis of rotation, then from equation (3) where the gravitational acceleration, g, is replaced by centrifugation acceleration, $a_c$, the capillary pressure is related to r, as $$\frac{dP_c}{dr} = \Delta \rho a_c \quad (8)$$

where $\Delta\rho$ is the density difference between the wetting fluid and the non-wetting fluid. The differential equation can be solved by simple integration $$\int_{P_{c2}}^{P_c} dP_c = \int_{r_2}^{r} \Delta\rho a_c \, dr = -\int_{r_2}^{r} \Delta\rho \omega^2 r \, dr \quad (9)$$

$$P_c(r) = \frac{1}{2}\Delta\rho\omega^2(r_2^2 - r^2) + P_{c2} \quad (10)$$

If the Hassler-Brunner boundary condition is adopted for the outlet end-face, i.e., the capillary pressure at the outlet end-face of the core is assumed to be zero, i.e., $P_{c2}=0$, then $$P_c(r) = \frac{1}{2}\Delta\rho\omega^2(r_2^2 - r^2) \quad (11)$$

and for a continuous phase, the capillary pressure at the inlet face of the core is $$P_{cL}(r) = P_c(r_1) = \frac{1}{2}\Delta\rho\omega^2(r_2^2 - r_1^2) \quad (12)$$

The next step of the method is to establish the relationship between the capillary pressure and fluid saturation S for a given core in the equilibrium state, i.e., $S=S(P_c)$. The capillary pressure thus calculated corresponds to the fluid saturation at the inlet end-face. This saturation should be calculated from the capillary pressure and the measured average fluid saturation.

The conventional method measures the rotational speed, $\omega$, and the average fluid saturation, $\overline{S}$, within the core.

However, the average fluid saturation, i.e., the ratio of liquid volume remaining after centrifugation to pore volume can be written as $$\overline{S} = \frac{1}{r_2 - r_1} \int_{r_1}^{r_2} S(r) \, dr \quad (13)$$

A relationship of saturation as a function of capillary pressure, $S=S(P_c)$ can be defined, so Eq. (13) can be expressed as follows by changing the integration variable $$P_c(r2)=0 \text{ and } P_c(r1)=P_c L$$

$$\overline{S} = \frac{1}{r_2 - r_1} \int_{P_{cL}}^{0} \frac{S(P_c)}{-\Delta\rho\omega^2 r} \, dP_c \quad (14)$$

An expression for r is obtained from Eq. (9)

$$r = r_2 \sqrt{1 - \frac{P_c}{\frac{1}{2}\Delta\rho\omega^2 r_2^2}} \quad (15)$$

and we obtain $$\overline{S} = \frac{1}{(r_2 - r_1)\Delta\rho\omega^2 r_2} \int_0^{P_{cL}} \frac{S(P_c)}{\sqrt{1 - \frac{P_c}{\frac{1}{2}\Delta\rho\omega^2 r_2^2}}} \, dP_c \quad (16)$$

with additional mathematical manipulation, this yields the Hassler-Brunner integral equation $$\overline{S} P_{cL} = \cos^2(\alpha/2) \int_0^{P_{cL}} \frac{S(P_c)}{\sqrt{1 - \frac{P_c}{P_{cL}}\sin^2\alpha}} \, dP_c \quad (17)$$

where $$\cos\alpha = \frac{r_1}{r_2}$$

$$\cos^2(\alpha/2) = (1 + \cos\alpha)/2 = \frac{r_1 + r_2}{2r_2}$$

and $$\sin^2\alpha = 1 - \cos^2\alpha = 1 - \frac{r_1^2}{r_2^2}$$

Equation 17 cannot be directly solved for the unknown function S. As pointed out by Hassler and Brunner, for small values of α (short core), the acceleration gradient along the core can be neglected. Assuming $r1/r2 \approx 1$, then $$\cos^2(\alpha/2)=1 \text{ and } \sin^2 \alpha=0$$

It should be emphasised that this assumption conflicts with other two assumptions from section 1.0.

Equation 17 is then reduced to $$\overline{S}P_{cL} = \int_0^{P_{cL}} S(P_c) dP_c \quad (18)$$

whose differential form is $$S_L = \frac{d}{dP_{cL}}(\overline{S}P_{cL}) \quad (19)$$

The value of $P_{Cl}$ for each centrifuge speed is then computed from Eq. (12), and the average saturation for each core is obtained from the dry and saturated weights and the corresponding stroboscope reading.

FIG. 3A shows a typical $\overline{S}P_{cL}$ as a function of $P_{Cl}$ and points indicated on the curve are the first, second and third speed etc. The value of saturation that corresponds to each value of $P_{Cl}$, which now represents the capillary pressure, is obtained from this curve by graphical differentiation according to Eq. (19). A typical plot of $P_c$ as a function of S is shown in FIG. 3B.

Equation (19) is an approximate solution introduced by Hassler and Brunner. Based on Equation (17), a number of other approximate solutions have been developed and used to determined capillary pressure curves. These methods have been reviewed by Ruth and Chen in D. Ruth and Z. Chen, The Log Analyst 36, 21 (1995), as well as Forbes in P. L. Forbes, Proceedings of the International Symposium of the Society of Core Analysts, Calgary, Sep. 8-10, (1997).

However, in 1993, a survey on centrifuge capillary pressure measurements was conducted by the Society of Core Analysts to evaluate how the different methods of implementing the centrifuge technique impact the results. The results of the survey were analyzed and discussed by Ruth and Chen. This survey revealed many problems with respect to designing and performing a centrifuge experiment and interpreting the experimental data.

As indicated above, a complete capillary pressure curve usually requires about 15 speeds and may take one to several days to acquire. Several samples are generally run simultaneously. A very low rotational speed is required to determine the entry pressure, especially, for high permeability samples, since wetting-phase saturation may drop dramatically at the first rotational speed. The minimum rotational speed is limited by the cut-off speed of the centrifuge. The SCA survey showed that wetting-phase saturation at the first rotational speed dropped dramatically from 100% to 50%, or even less than 30% for capillary pressure measurements. For low permeability samples, the limit on the highest rotational speed of centrifuge rotor may result in the loss of data on residual wetting phase saturation. This was a common occurrence in the SCA survey reports. Unfortunately, the requirement for minimum and maximum rotational speed results in a serious gravity effect and the violation of the outlet boundary condition, respectively, as discussed above. Therefore, the traditional centrifuge technique has a number of problems which would be desirable to solve.

SUMMARY OF THE INVENTION

According to the present invention, there is provided a method of measuring a parameter in a sample, comprising: mounting a sample for rotation about an axis such that different portions of the sample are spaced at different distances from said axis; rotating the sample about said axis; measuring a first parameter in said different portions of said sample, and determining the value of a second parameter related to the force to which each portion is subjected due to said rotating of said sample.

Also according to the present invention, there is also provided an apparatus for measuring a parameter in a sample, comprising: a sample holder for rotating a sample about an axis such that different portions of said sample are spaced at different distances from said axis; measuring means for measuring a first parameter in said different portions of said sample, and generating means for generating data comprising the values of said first parameter and associated with each value, the value of a second parameter relating to the force to which each portion is subjected due to rotation of said sample about said axis.

The present invention is predicated on the recognition that the force to which a rotating body or sample is subjected varies as a function of distance from the rotational axis, and exploits this principle to measure one or more parameters in a sample such as fluid distribution as a function of a parameter related to centrifugal force, such as capillary pressure. Therefore, rather than varying the angular velocity to obtain a variable force, embodiments of the present invention maintain the angular velocity constant and "vary" the force by varying the distance from the rotational axis at which the desired parameter(s) is/are measured.

In some embodiments, the sample comprises solid material and a material capable of movement relative to the solid material when subjected to a force. For example, the sample may comprise a porous material and the movable material may comprise a fluid.

In some embodiments, the step of measuring the first parameter comprises measuring the parameter by imaging the portions of the sample. The imaging may comprise magnetic resonance imaging, for example single-point magnetic resonance imaging, single-point ramped magnetic imaging, single-point ramped magnetic imaging with $T_1$ enhancement, centric scan single-point ramped magnetic imaging, spiral scan single-point ramped magnetic imaging or any other suitable technique.

In some embodiments, the first parameter is indicative of the fluid content, i.e. the amount of fluid in the portions of the sample.

In some embodiments, the second parameter comprises any one of capillary pressure, acceleration, force and the distance of each portion relative to the axis.

In some embodiments, the sample contains a first fluid prior to the measuring step, and the method further comprises exposing the sample to a second fluid for introduction into the sample during the rotating step. The first fluid may be different from the second fluid, and in some embodiments, the technique for measuring the first parameter and/or the fluids are selected so that the measurements discriminate between the fluids allowing the first parameter of one of the fluids to be measured. In one embodiment, the fluids may comprise heavy water and oil, respectively, and the measuring technique chosen so that the oil distribution in the sample can be measured as distinct from the heavy water distribution. This technique is particularly useful when conducting primary drainage, imbibition and secondary drainage measurements, for example on reservoir rock.

In some embodiments, the step of mounting the sample for rotation comprises mounting the sample such that a portion of the sample extends either side of the rotational axis. For example, the sample may be disk-shaped with the axis of the disk coaxial with the axis of rotation. Advantageously, this arrangement allows the sample and centrifuge to be more compact along the radial direction than the rotor components and sample holder assembly of a conventional centrifuge. This also allows the centrifuge to be mounted in an MRI instrument obviating the need to remove the sample from the centrifuge in order to make MRI measurements. As the radius of the rotating parts can be less, vibration and frictional heating can also be reduced. In addition, the use of a disk-shaped sample allows 2D MRI measurements to be made increasing the signal-to-noise ratio. Furthermore, the use of a circular disk eliminates radial effects on the measurement.

Embodiments of the present invention provide a simple methodology which requires only a single moderate centrifuge speed, readily achievable on a low cost desktop centrifuge. Unlike the conventional methods, the present methodology does not require measuring the fluid expelled from a core. Embodiments of the method recognize that the centrifugal pressure varies longitudinally along the core, which leads to a variable longitudinal fluid saturation. Embodiments of the method measure the fluid remaining inside the core, spatially resolved along the length of the core (or radius for a disk-shaped sample), after centrifugation. The spatially resolved fluid saturation measurement can be rapid and, in some embodiments, uses MRI technology developed by the University of New Brunswick MRI Centre. The measurement may be implemented on a low cost, low field, permanent magnet based desktop MRI instrument.

Advantageously, the method of embodiments of the present invention allow the capillary pressure curve to be measured using a single-speed centrifuge experiment and one dimensional magnetic resonance imaging for porous media, such as rock core samples. Embodiments of the method are rapid, accurate, and relatively inexpensive. The method can be rapid because centrifugation is required at only one centrifuge speed. With a one dimensional saturation profile determined by MRI, a complete capillary pressure curve, with approximately 40 data points can obtained. The process can be approximately 15 times faster than a traditional measurement with 15 data points, corresponding to 15 centrifuge speeds. The measurement is accurate, because there are no assumptions of linearity for the centrifugal field over the length of a core plug. Since a single, moderate centrifuge speed can be employed, the speed can be set so that the effect of gravity will be very small and the outlet boundary condition of the core plug (or disk) can be satisfied. In addition, friable and unconsolidated rock samples may be used with embodiments of the method, since extreme rotational speeds are not required. The measurements may be performed using only a small and inexpensive desktop centrifuge and a desktop permanent magnet based one dimensional MRI system, although any other suitable MRI instrument and measuring technique could be used, including 2D and 3D imaging.

According to an aspect of the present invention, there is provided a method of measuring a parameter indicative of fluid content in a porous sample, comprising: mounting the porous sample for rotation about an axis such that different portions of the sample are spaced at different distances from the axis; rotating the sample about said axis at a substantially constant speed of rotation; measuring a first parameter indicative of fluid content in each of said different portions of said sample comprising detecting said fluid by one dimensional magnetic resonance imaging along the sample in the direction of spatial separation between the different portions thereof using a phase encoded magnetic field gradient to spatially resolve each portion along the sample, wherein said magnetic resonance imaging comprises one dimensional single-point ramped imaging, which includes the steps of: (a) progressively increasing the gradient of a magnetic field directed in a first direction from zero to a predetermined maximum value; (b) applying to the sample an RF pulse at each of a number of different values of magnetic field gradient between zero and said predetermined maximum value; (c) detecting a nuclear magnetic resonance (nmr) signal from the sample resulting from each excitation pulse to provide a first set of data comprising respective values of magnetic field gradient and the respective values of the detected nmr signal from the sample; (d) after said magnetic field gradient reaches said predetermined maximum in said first direction, reducing said field gradient to zero without applying an RF pulse to said sample; (e) progressively increasing the gradient of a magnetic field directed in a second direction opposite to said first direction from zero to a predetermined maximum value; (f) applying an RF excitation pulse to the sample at each of a number of different values of magnetic field gradient between zero and said predetermined maximum value; (g) detecting a nuclear magnetic resonance signal from said sample resulting from each excitation pulse to provide a second set of data comprising respective values of magnetic field gradient and the respective values of the detected nuclear magnetic resonance signal from the sample; and (h) determining the values of said first parameter at said different positions along the sample from the first and second sets of data; and determining the value of a second parameter related to the force to which each portion is subjected due to said rotating of said sample.

According to another aspect of the present invention, there is provided a method of measuring a parameter indicative of fluid content in a porous sample, comprising: measuring a parameter indicative of fluid content in each of a number of different portions of said sample comprising detecting said fluid by one dimensional magnetic resonance imaging along the sample in the direction of spatial separation between the different portions thereof using a phase encoded magnetic field gradient to spatially resolve each portion along the sample, wherein said magnetic resonance imaging comprises one dimensional single-point ramped imaging, which includes the steps of: (a) progressively increasing the gradient of a magnetic field directed in a first direction from zero to a predetermined maximum value; (b) applying to the sample an RF pulse at each of a number of different values of magnetic field gradient between zero and said predetermined maximum value; (c) detecting a nuclear magnetic resonance (nmr) signal from the sample resulting from each excitation pulse to provide a first set of data comprising respective values of magnetic field gradient and the respective values of the detected nmr signal from the sample; (d) after said magnetic field gradient reaches said predetermined maximum in said first direction, reducing said field gradient to zero without applying an RF pulse to said sample; (e) progressively increasing the gradient of a magnetic field directed in a second direction opposite to said first direction from zero to a predetermined maximum value; (f) applying an RF excitation pulse to the sample at each of a number of different values of magnetic field gradient between zero and said predetermined maximum value; (g) detecting a nuclear magnetic resonance signal from said sample resulting from each excitation pulse to provide a second set of data comprising respective values of magnetic field gradient and the respective values of the detected nuclear magnetic resonance signal from the sample; and (h) determining the values of said parameter at said different positions along the sample from the first and second sets of data. According to another aspect of the present invention, there is provided an apparatus for measuring a parameter indicative of fluid content in a porous sample comprising a magnetic resonance imaging system which includes a magnet for applying a static magnetic field to said sample, an RF pulse generator for applying RF excitation pulses to said sample, a detector for detecting magnetic induction signals from the sample, a generator for applying a magnetic field gradient to the sample and a controller for controlling the magnetic field gradient, wherein the magnetic resonance imaging system is operable to perform one dimensional single-point ramped imaging, in which said gradient controller is operative to progressively increase the gradient of a magnetic field directed in a first direction from zero to a predetermined maximum value; the RF pulse generator is operative to apply to the sample an RF pulse at each of a number of different values of magnetic field gradient between zero and said predetermined maximum value; said detector is operative to detect a nuclear magnetic resonance (nmr) signal from the sample resulting from each excitation pulse to provide a first set of data comprising respective values of magnetic field gradient and the respective values of the detected nmr signal from the sample, the magnetic field gradient controller being operative to reduce the field gradient to zero after said magnetic field gradient reaches said predetermined maximum in said first direction without applying an RF pulse to the sample and progressively increasing the gradient of a magnetic field directed in a second direction opposite to the first direction from zero to a predetermined maximum value; the RF pulse generator being operative to apply an RF excitation pulse to the sample at each of a number of different values of magnetic field gradient between zero and said predetermined maximum value, said detector being operative to detect a nuclear magnetic resonance signal from the sample resulting from each excitation pulse to provide a second set of data comprising respective values of magnetic field gradient and the respective values of the detected nuclear magnetic resonance signal from the sample, and determining means for determining the values of the parameter indicative of fluid content at said different positions along the sample from the nmr signals in the first and second sets of data.

According to another aspect of the present invention, there is provided an apparatus comprising a magnetic imaging system and a sample holder rotatably mounted in said magnetic imaging system.

Also according to this aspect of the invention, there is provided a method comprising rotatably mounting a sample in a magnetic imaging system, rotating said sample to subject the sample to a centrifugal force, and measuring a parameter in said sample.

Advantageously, this arrangement allows a sample to be conditioned in a centrifuge and then measured using MRI, while the sample is situ in the centrifuge.

BRIEF DESCRIPTION OF THE DRAWINGS

Examples of embodiments of the present invention will now be described with reference to the drawings, in which:

FIG. 1b shows a top view of the centrifuge apparatus shown in FIG. 1a;

FIG. 3b shows an example of a $S-P_c$ curve derived from FIG. 3a.

FIG. 6 shows a data structure according to an embodiment of the present invention;

DESCRIPTION OF EMBODIMENTS

Figure 1A:
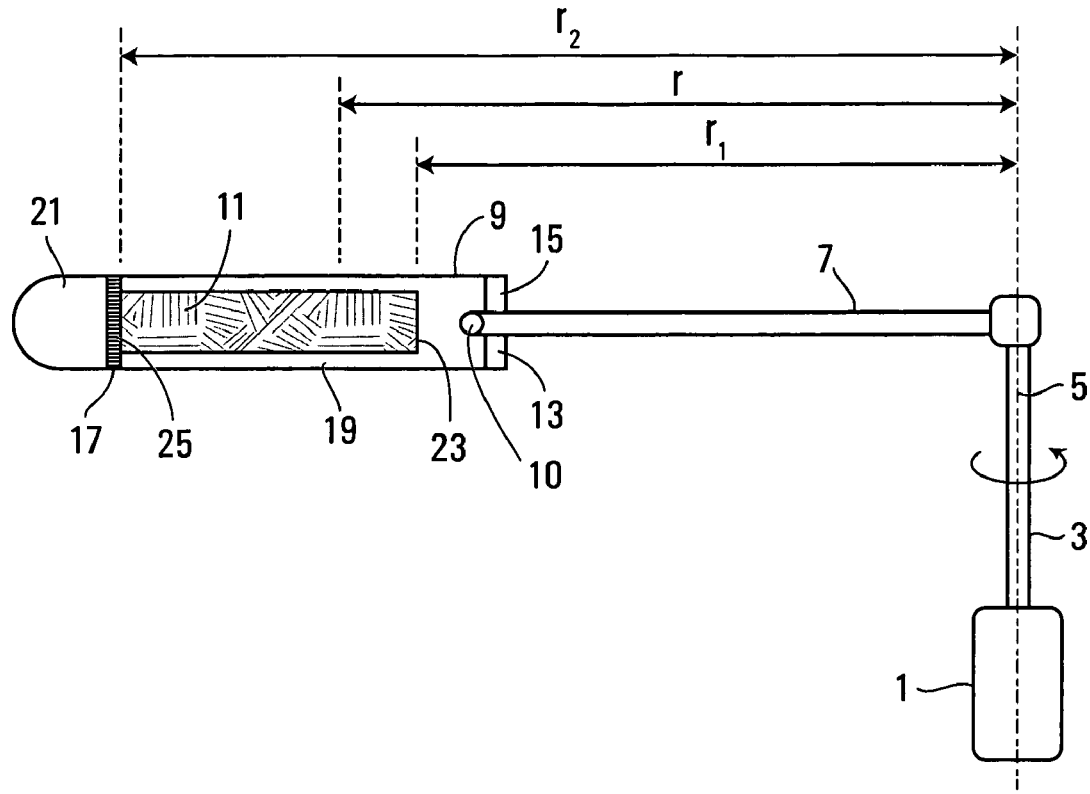
FIG. 1a shows a side view of a centrifuge apparatus.
Figure 1B:
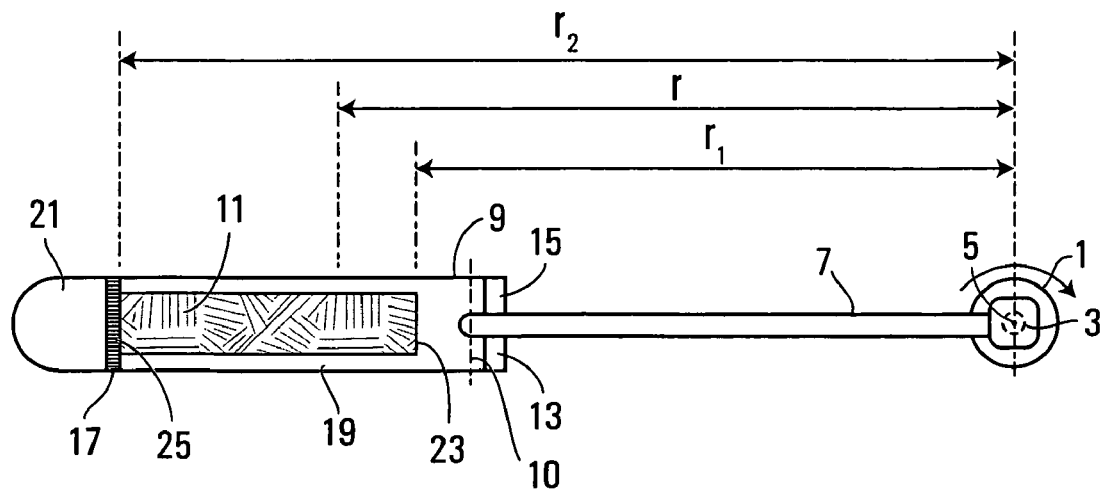
Figure 2:
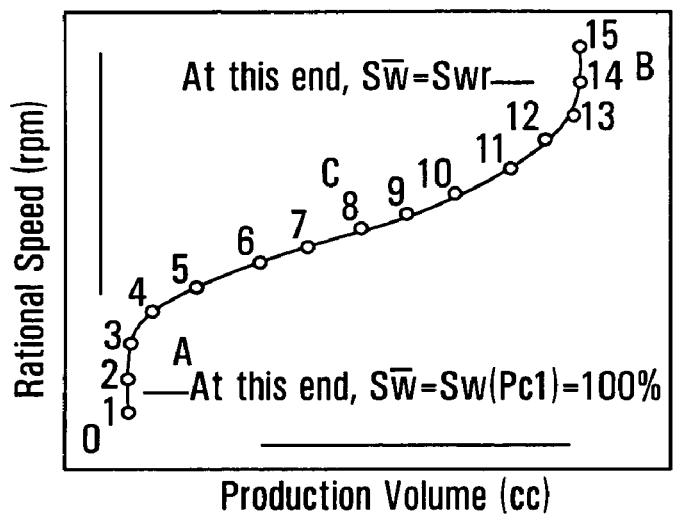
FIG. 2 shows a set of experimental data points of rotational speed and production volume for a traditional method.
Figure 3A:
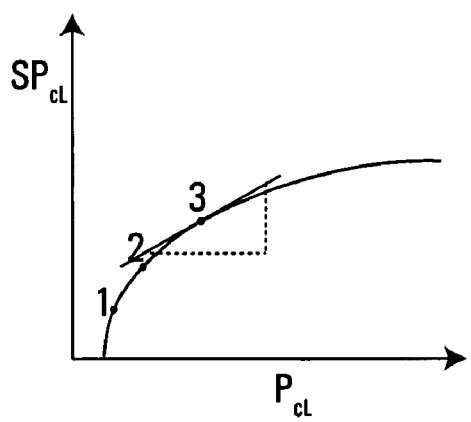
FIG. 3a shows an example of a $\overline{SP}_{cL-P_{cL}}$ curve from a conventional measurement technique.
Figure 3B:
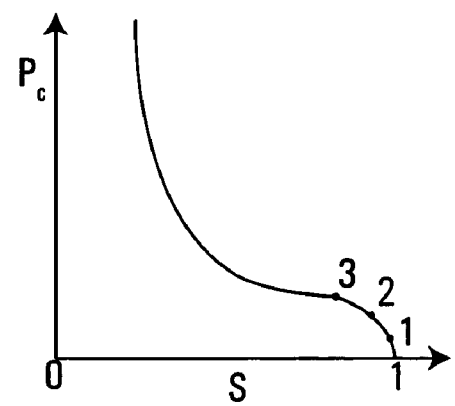

FIGS. 1 *a* and 1 *b* show a schematic diagram of a centrifuge for use in spinning a sample as part of a capillary pressure measurement, as described above, and which may be used in apparatus and methods of embodiments of the invention. The centrifuge comprises a motor 1 having a shaft 3 which rotates about a rotational axis 5, an arm 7 extending from the shaft 3 and a sample holder 9 pivotally connected to the arm 7 about a pivotal connection point 10 at the end 15 of the arm, so that the sample holder is free to swing up and down. The sample holder comprises a removable sealed end part or closure 13 at the inner end 15 and a porous plate 17 which divides the interior of the sample holder into a first chamber 19 for containing a porous sample and a second chamber 21 at the distal end thereof for collecting liquid 22 expelled from the sample through the porous plate 17.

The sample has an inlet face 23 spaced at a distance $r_1$ from the rotational axis 5 and an outlet face 25 spaced at a distance $r_2$ from the axis 5. r is the distance of any point in the sample from the rotational axis.

Figure 4A:
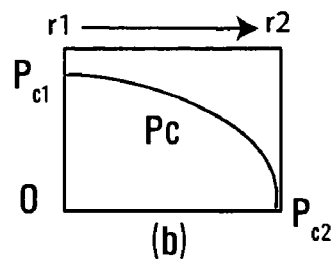
FIG. 4a shows a capillary pressure distribution along the length of a sample.
Figure 4B:
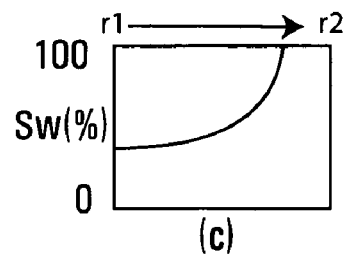
FIG. 4b shows a graph of the water saturation distribution along the length of a sample.

FIG. 4*a* shows a graph of the capillary pressure distribution along the length of the sample between $r_1$ and $r_2$ (i.e. the inlet and outlet faces of the sample) after the sample has been spun in the centrifuge, and FIG. 4*b* shows a graph of the water saturation distribution along the length of the sample.

In a conventional centrifuge experiment, a liquid saturated core plug, confined in the holder, is spun at different rotational speeds. The core holder contains another fluid which replaces the fluid displaced from the core. In the simplest case this fluid is air and it displaces water from an initially saturated core. The fluid saturation S is written as Sw in FIG. 4*b*.

The longitudinal water saturation of the core, varies from a low level at the inlet end-face, where the capillary pressure is a maximum, to a maximum water saturation of 100% at the outlet end-face, where the capillary pressure is zero, as shown in FIGS. 4*a* and 4*b*, respectively. The longitudinal fluid saturation distribution can not be directly determined with traditional measurements, which must assume a model saturation function, as described above.

The method of the present invention does not need to assume a model saturation function. If a cylindrical core of length L is subjected to an acceleration $a_c = \omega^2 r$, where $\omega$ is the angular velocity of the centrifuge and r is the distance from the axis of rotation, then the gradient of capillary pressure is determined by Eq. 8, where $\Delta\rho$ is the density difference between the wetting and non-wetting fluids. Integration over distance r, with the capillary pressure assumed to be zero at the outlet end, $P_{c2} = 0$, yields a simple prediction of the variation of the capillary pressure as a function of distance r, according to Eq. 11.

The fluids involved determine the density difference, and the centrifuge determines $\omega$ and r. Embodiments of the present invention provide a method of determining the saturation S as a function of r and provide the capability to directly determine $P_c(r)$ as a function of $S(r)$ which is the capillary pressure curve.

The fluid saturation, S, may be measured by using any suitable technique, for example imaging techniques such as magnetic resonance imaging. Any suitable, conventional MRI imaging system may be used, for example a commercially available MRI system having superconducting magnets which are capable of generating relatively large static magnetic fields, or a smaller MRI instrument, for example a desktop mounted instrument which uses non-superconducting magnets to generate the static magnetic field, an example of which is shown in FIG. 5.

Figure 5:
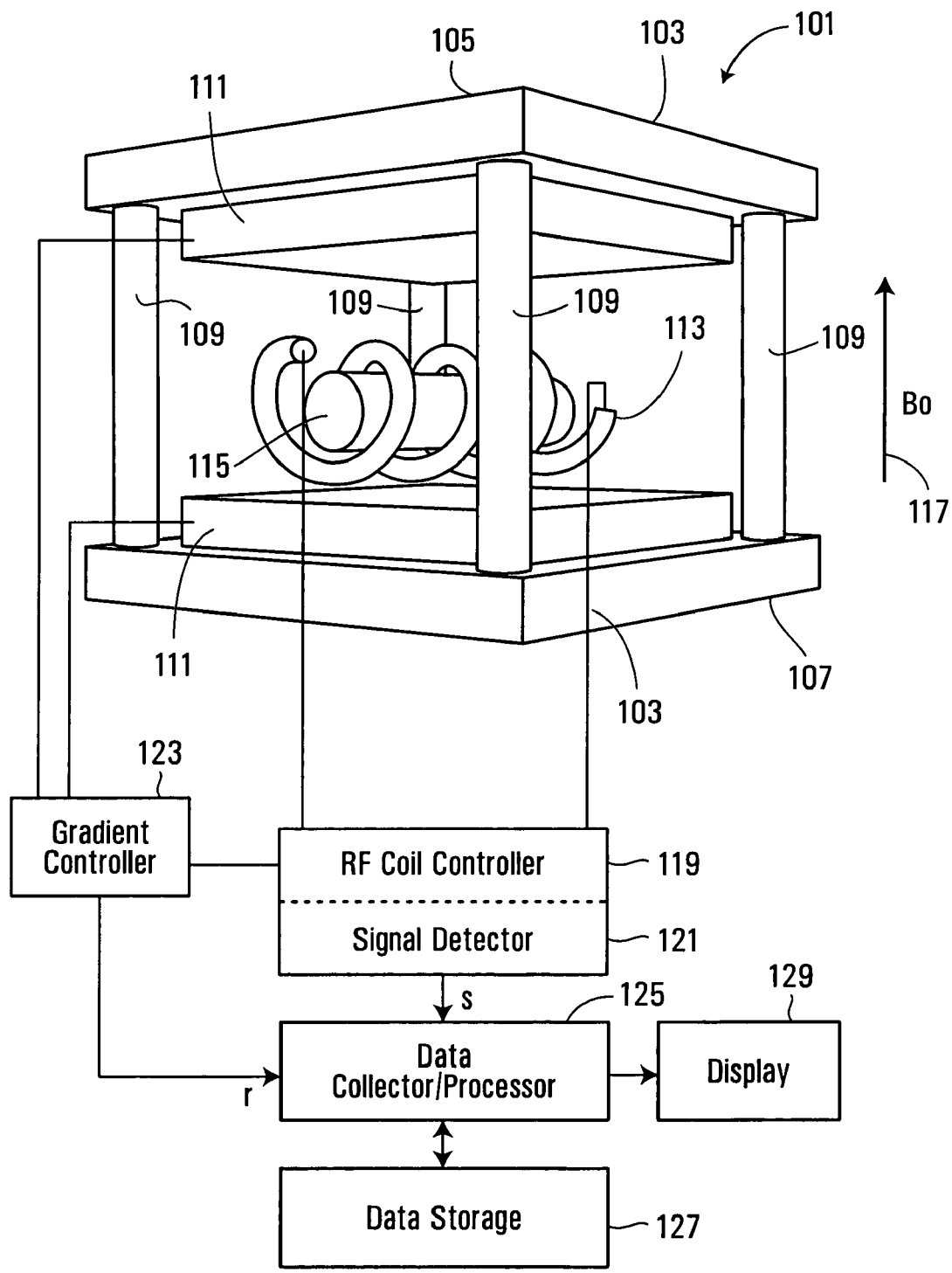
FIG. 5 shows a schematic diagram of an MRI measurement system.

FIG. 5 shows a schematic diagram of an imaging system comprising a low field permanent magnet and gradient set, as well as an RF coil system for MRI measurements. The imaging system 101 comprises a permanent magnet having spaced apart magnetic pole pieces 105, 107, spacers (e.g., pillars) 109 separating the magnetic pole pieces 105, 107, a gradient set 111, and an RF coil 113 which surrounds a sample (for example, a rock core sample) 115. The arrow 117 shows the direction of the magnetic field, $B_0$. The RF coil and gradient set 111 are connected to external control circuits.

The imaging system further comprises an RF coil controller 119 for generating and delivering RF pulses to the coil, and a signal detector 121 for detecting the magnetic induction signal from the coil. A gradient controller is provided for controlling the field gradient and supplies gradient control signals to each coil of the gradient set for scanning. The gradient set may include coils for scanning in any one or more of the x, y and z directions. The imaging system includes a data collector/processor 125 for receiving data from the signal detector 121 and gradient controller 123, a memory 127 for data storage, and an optional display 129.

The gradient controller provides data to the data collector/processor unit 125 which is indicative of the scan position along the sample core, e.g. the value of r or data from which the value of r can be determined. Using this information, the data processor can determine the values of capillary pressure from equation 11.

The signal detector provides a signal or data to the data collector indicative of a parameter of the detected magnetic induction signal from the RE coil and from this information determines the relative saturation of the sample. It has been found through experiment that the intensity of the free induction decay signal is substantially proportional to the local water content and therefore a measurement of the ratio of the intensity of the signal after centrifugation to the intensity of the signal when the sample is saturated provides a measurement of the relative fluid saturation. An example of an MRI measurement technique which may be used to measure the relative fluid saturation is described in detail below.

Generally, values of the measured parameter, such as fluid content, in different portions of the sample may be acquired and processed using any suitable technique, and the data acquisition system shown in FIG. 5 is just one example. Data collected and/or processed by the data collector/processor 125 such as values of capillary pressure and relative fluid content may be stored in the memory. A visual representation of the data, for example a two-dimensional plot may optionally be generated and presented on the display 129 or a printer (not shown).

An example of a data structure containing correlated values of the first and second parameters which may be stored in a memory such as the memory 129 shown in FIG. 5, or another storage device, is shown in FIG. 6. In this data structure 151, the first parameter 153 comprises, for example a parameter related to fluid content in the sample measured at different distances from the axis of rotation, and the second parameter 155 is related to the force to which each portion of the sample at which the first parameter is measured is subjected due to rotation about the rotational axis and may comprise, for example, capillary pressure.

In one embodiment, a quantitative pure phase encode MRI methodology developed by University of New Brunswick is used to measure the local fluid content in a core prior to centrifugation, and then immediately following centrifugation.

The standard SPRITE (single-point ramped imaging with $T_1$ enhancement) imaging technique has proven to be a very robust and flexible method for the study of a wide range of systems with short relaxation times. This method is described in Balcom, B. J., MacGregor, R. P., Beyea, S. D., Green, D. P., Armstrong, R. L. and Bremner, T. W. "Single Point Ramped Imaging with T1 Enhancement (SPRITE)", *J. Magn. Res. A* (1996) 123, 131-134, the entire content of which is incorporated herein by reference. As a pure phase encoding technique, SPRITE is largely immune to image distortions generated by susceptibility induced magnetic field variation, chemical shift, and paramagnetic impurities. Repetitive excitation and acquisition are performed in the presence of ramped or stepped phase encoding gradients, which enable systems with $T_2^*$ lifetimes as short as tens of microseconds to be successfully visualized.

The standard SPRITE technique is however a longitudinal steady state imaging method, the image intensity is related to the longitudinal steady state, which not only decreases the signal-to-noise ratio, but also introduces many parameters into the image signal equation, such as the repetition time, spin-lattice relaxation time, RF flip angle, as well as the phase encoding time, effective spin-spin relaxation time, and spin density.

A centric scan strategy for SPRITE imaging removes the longitudinal steady state from the image intensity equation, and increases the inherent image intensity, as described in Mastikhin, I. V., Balcom, B. J., Prado, P. J. and Kennedy, C. B. "SPRITE MRI with Prepared Magnetization and Centric k Space Sampling", *J. Magn. Res.* (1999) 136, 159-168, the entire content of which is incorporated herein by reference. The image signal intensity, with appropriate conditions, no longer depends on the spin lattice relaxation time and the repetition time. These features of centric scan SPRITE make it an ideal method for quantitative imaging of short relaxation time species in porous media.

Double Half k-Space 1D MRI

For a conventional full k-space SPRITE method, data acquisition starts from one extremity of k-space (Gmax) then increments to the other extremity of k-space (−Gmax). The center of k-space is sampled when the longitudinal magnetization approaches the steady state, with the signal intensity given by $$S = M_0 \frac{1-E}{1-CE} \exp\left(-\frac{t_p}{T_2^*}\right) \sin\alpha \qquad (20)$$

Where $M_0$ is the equilibrium magnetization, $C=\cos\alpha$, $\alpha$ is the RF flip angle, $E=\exp(-TR/T_1)$, $t_p$ is the phase encoding time, $T_2^*$ is the effective spin-spin relaxation time, and $\alpha$ is the flip angle.

Figure 7:
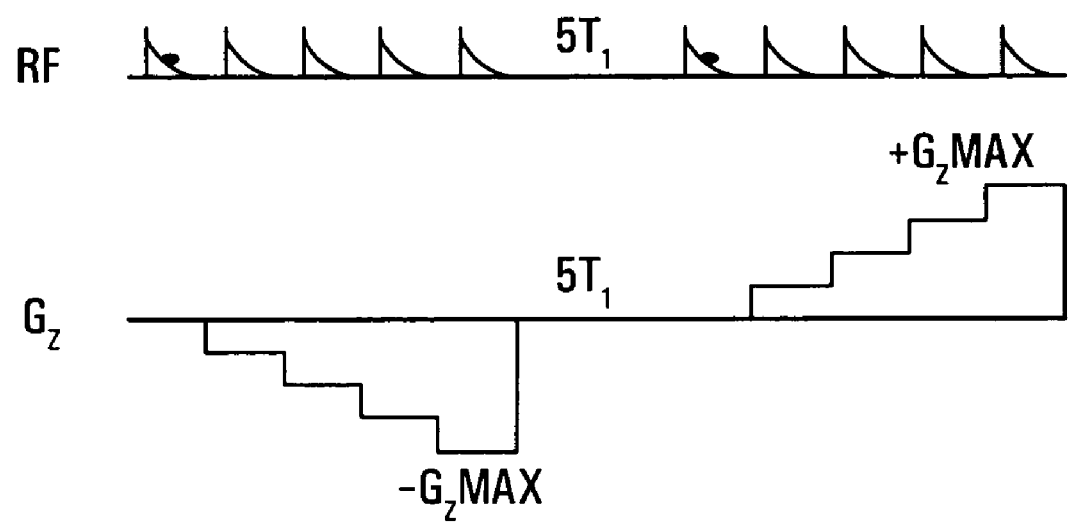
FIG. 7 shows a representation of RF pulses and field gradients used to perform double half k-space SPRITE imaging.

In order to remove the effect of the longitudinal steady state, second term of Eq. (20), from the signal intensity, a double half k-space technique is introduced. In this technique as shown in FIG. 7, the k-space data are collected sequentially from '0' to '−$k_z$', corresponding to a gradient change from 0 to minus maximum gradient (−Gmax), after a delay, for example of about 5 times $T_1$ or longer, the other of half k-space data is sampled from '0' to '+$k_z$', corresponding to a gradient change from 0 to a maximum gradient (Gmax). In the centric scan SPRITE method, the observable local sample magnetization (S) is given by:

$$S = M_0 \exp\left(-\frac{t_p}{T_2^*}\right) \sin\alpha \qquad (21)$$

where $M_o$ is the equilibrium magnetization, $t_p$ is the phase encoding time, $T_2^*$ is the effective spin-spin relaxation time, and $\alpha$ is the flip angle. $M_o$ is proportional to local fluid content. Centric scan SPRITE methods are naturally spin-density weighted.

In a 1D centric scan SPRITE profile, the local image intensity ($S_{image}$) is given by Eq. 20, where $M_o(r)$ is the equilibrium magnetization which is proportional to local fluid content, $t_p$ is the phase encoding time, $T_2^*$ is the effective spin-spin relaxation time, and $\alpha$ is the RF flip angle. The trigonometric term is a constant; if $t_p$ is $<<T_2^*$ the local image intensity is directly proportional to the local fluid content. If the phase encode time $t_p$ is not $<<T_2^*$ (typically hundreds of usec in realistic porous materials) the local image intensity is still proportional to the local fluid content since it has been observed that $T_2^*$ is usually single exponential in realistic porous media (unlike the time constant $T_2$), and invariant with the local fluid content. The local saturation in the core S(r) is thus determined by taking the ratio of the MRI image of the core after centrifugation, and before centrifugation, $S(r)=S_{image(r)after}/S_{image(r)before}$.

For the double half k-space SPRITE imaging pulse sequence, repetitive RF excitation and data acquisition is performed in the presence of a ramped phase encoding gradient, in this case, $G_z$. A single short duration RF pulse is applied after the magnetic field gradient has been switched and allowed to stabilize for each step. As the RF pulse is applied in the presence of a magnetic field gradient, its duration must be short enough to irridate the overall distribution of frequencies introduced by the gradient. After a fixed duration phase encoding time, $t_p$, a single complex datum point is acquired on the NMR free induction decay signal. The gradient changes from 0 to minus maximum gradient (-$G_z$max), after a delay of five times of $T_1$, the gradient changes from 0 to maximum gradient ($G_z$max). After each repitition time TR, the value of the applied gradient, $G_z$, is incremented for one-dimensional sampling. Sixty four steps, each on the order of 1 ms duration of TR may typically employed, although any other number of steps may be used. The image is reconstructed with Fourier transformation of the spatially encoded experimental data.

A Single Exponential of FID

For rocks, experimental results show the NMR line broadening is frequently dominated by the effect of internal magnetic field distortions induced by susceptibility differences between the pore fluid and the solid matrix. The free induction decay (FID) is frequently observed to be single exponential, with the spin-spin relaxation time ($T_2$) decay usually multi-exponential. Proton-density imaging is readily obtained with equation (22) by single exponential fitting the FID data from a series of Centric Scan SPRITE images with variable encoding times, $t=t_p$.

Figure 8:
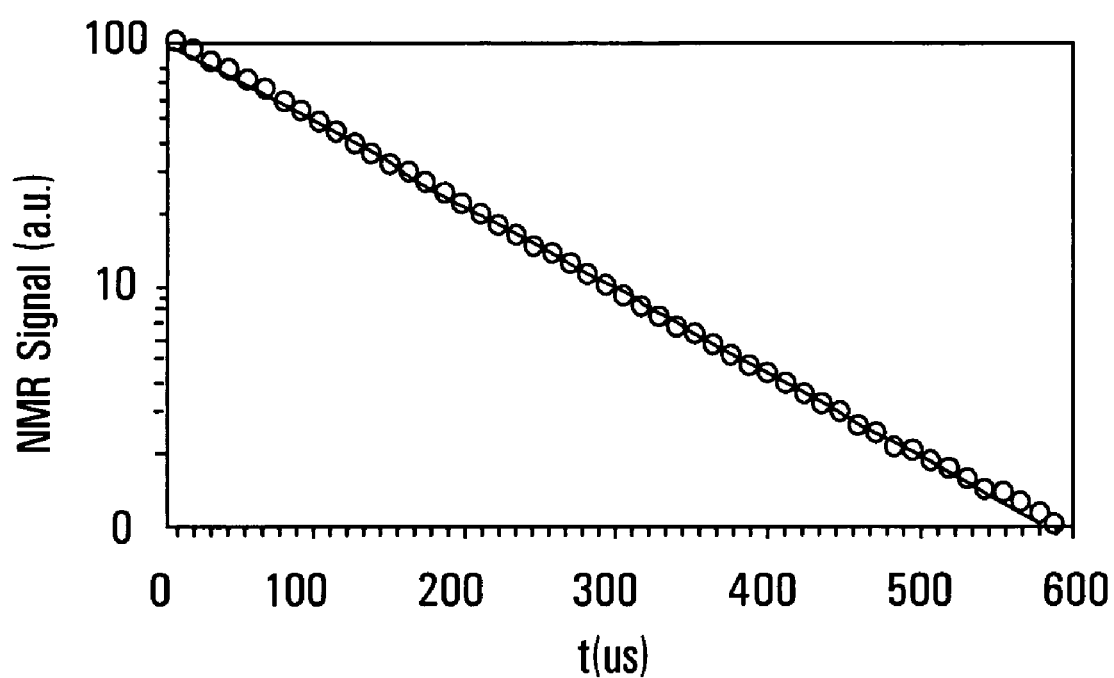
FIG. 8 shows a semi-logarithmical plot of free induction decay (FID) for a fully water saturated Berea sandstone.

FIG. 8 shows an example of a semi-logarithmical decay curve of the NMR signal, observed after a 90 degrees RF pulse. The data was fitted to the equation:

$$S = M_0 \exp(-t/T_2^*) \tag{22}$$

Where S is the NMR signal intensity, $M_0$ is the equilibrium sample magnetization, t is the acquisition time, and $T_2^*$ is the effective spin-spin relaxation time. The fit $T_2^*$ was 127 µs. The FID has a single exponential decay over 2 orders of signal intensity. In experiments carried out by the inventors, the value of $T_2^*$ of the Berea sandstone samples examined varied from 114 µs to 127 µs when the water saturation was varied from 9.1% to 100%. For Centric Scan SPRITE images with a $t_p$ of 30 µs, assuming the term $\exp(-t/T_2^*)$ is constant in Equation (22) with water saturation changes, causes a relative error of less than 2%. Under these experimental conditions, Centric Scan SPRITE images are essentially proton-density images. The single exponential decay of the FID at different water and air saturation, with $T_2^*$ largely insensitive to water and air saturation, has been observed for many sedimentary rocks.

This feature makes it easy for centric scan SPRITE to obtain spin density imaging two ways: (1) ensure the phase encoding time is much shorter than $T_2^*$ for longer $T_2^*$ samples; (2) acquire multiple FID data points and fit the data sets with a single exponential with equation (22) for a range of phase encoding times to reconstruct spin density images with extrapolated data.

For the measurement of water saturation of rocks after centrifugation, 1D double half k-space SPRITE image intensity before and after centrifuge can be expressed as $$M = M_0 \exp\left(-\frac{t_p}{T_2^*}\right) \sin \alpha \tag{23}$$

$$M = M_{0a} \exp\left(-\frac{t_p}{T_{2a}^*}\right) \sin \alpha \tag{24}$$

where M and $M_a$ are the observable local sample magnetization before and after centrifugation, respectively. $M_o$ and $M_{oa}$ are the equilibrium sample magnetizations before and after centrifugation, respectively. $T_2^*$ and $T_{2a}^*$ are the effective spin-spin relaxation times before and after centrifugation, respectively.

The water saturation after centrifuge can be calculated from equation (24) divided by equation (23). The calculated water saturation ($S_w$) is therefore $$S_w = \frac{M_a}{M} = \frac{M_{0a}}{M_0} \exp\left(\frac{t_p}{T_2^*} - \frac{t_p}{T_{2a}^*}\right) \tag{25}$$

As $T_{2^*}$ is approximately independent of changes of water saturation in sedimentary rocks, the exponential term in equation (25) is approximately equal to 1. So, the direct ratio of the water content profiles can be used to calculate the spatially resolved water saturation along the length of the core.

The range of capillary pressure distribution in a sample may be increased either by increasing the length of the sample and/or increasing the rotational speed of the sample in the centrifuge.

In measuring the capillary pressure curve using a single speed, the rotational speed should be selected to be sufficiently large to ensure that an irreducible water saturation is reached at the inlet face of the sample core. The inventors have found that an estimate of the capillary pressure for irreducible water saturation may be obtained as follows.

The Leverett J function provides an approximation for the behaviour of rock samples based on numerous measurements and is given by the equation:

$$J = \frac{P_c}{\sigma \cos \theta} \sqrt{\frac{k}{\phi}} \tag{26}$$

where k is permeability, and $\phi$ is porosity.

Based on this function, the rotational speed, $\omega$, for reaching the irreducible water saturation ($S_{wi}$) may be estimated by the equation $$P_c(r_1) = \frac{1}{2} \Delta \rho \omega^2 (r_2^2 - r_1^2) \geq J(S_{wi}) \sigma \cos \theta / \sqrt{k/\phi} \tag{27}$$

or $$\omega^2 \geq \frac{2 J(S_{wi}) \sigma \cos \theta}{\Delta \rho (r_2^2 - r_1^2) \sqrt{k/\phi}} \tag{28}$$

Reasonable Leverett J values at irreducible water saturation, $J(S_{wi})$ are in the range of 3-4, as described in Brown H. W., Capillary pressure investigations, Trans. AIME, 192, 67 (1951).

The capillary pressure required to reach irreducible water saturation can be estimated using formula 27. Thus, for example, in a water and air system, the fluid contact angle $\theta=0$ degrees, $\sigma=72$ Mn/m, permeability k=0.18 µm², porosity $\phi=0.186$, and assuming $J(S_{wi})=3$, the required capillary pressure to reach the irreducible water saturation at the inlet face of the sample, $P_c(r_1) > 32.9$ Psi.

The rock sample for centrifuge capillary measurements is generally required to be homogenous, and magnetic resonance imaging can advantageously be employed to check the homogeneity of the sample.

The above method for determining the minimum speed for the centrifuge can be used in any application where it is desirable to determine this parameter.

Capillary Pressure Curve by Centrifuge and MRI

Specific examples of capillary pressure curve measurements for two rock samples using embodiments of the present method and apparatus are described below.

A cylindrical Berea sandstone and an oilfield sandstone rock core #125 were water saturated under vacuum conditions. For the Berea sandstone core, its porosity (the ratio of pore volume to bulk volume of rock) was 18.6%, with a permeability of 0.18 $\mu m^2$. The sample length was 52 mm with a diameter of 25 mm. For the sandstone core #125, the porosity was 27.6%, with a permeability of 0.372 $\mu m^2$. The sample length was 51.5 mm with a diameter of 25 mm.

The Berea sandstone samples employed in these MRI centrifugation experiments, and complementary mercury intrusion experiments, were extracted from the host rock in close proximity to one another. We thus assume they have a similar pore structure due to the homogeneity of the respective Berea sandstone formations.

The centrifugation experiments were carried out with a Beckman TJ6R tabletop centrifuge at 4° C. in air and at 1500 RPM for 2 hours for Berea sandstone and at 750 RPM for 35 minutes for rock #125. The centrifuge radius to the bottom of rock was 13.8 cm. The cylindrical surface of the core sample was wrapped with Teflon tape to ensure longitudinal fluid flow within the core.

All NMR experiments were performed in a 2.4T horizontal bore superconducting magnet (Nalorac Cryogenics Inc., Martinez, Calif.) with an Apollo console (Tecmag Inc., Houston, Tex.). For all NMR experiments, a proton-free 47 mm inner diameter eight-rung quadrature birdcage probe (Morris Instruments, Ottawa, ON) was employed. The core samples were wrapped with Teflon tape to decrease the evaporation of water within the samples during MRI measurements.

1D water content profiles of the rock before and after centrifugation were obtained by 1D double half k-space SPRITE MRI with a phase encoding time of 30 μs, flip angle α of 6 degrees, for a field of view of 9 cm, with an image matrix size of 64 points, nominal resolution 1.4 mm. Four signal averages were collected for a total scan time of 25 seconds.

Figure 9:
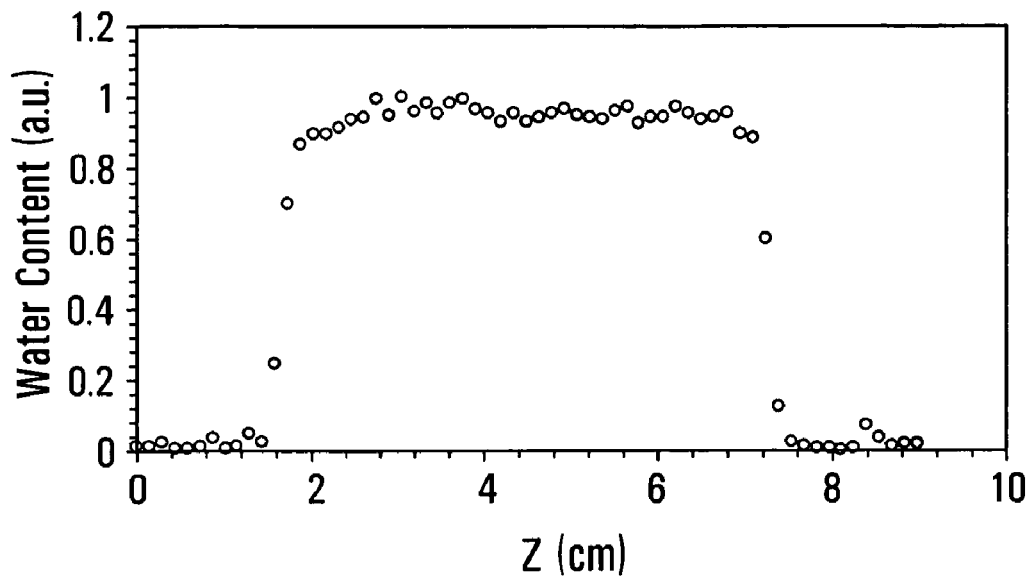
FIG. 9 shows a one dimensional water content distribution along the length of the Berea sandstone for 100% saturated state.
Figure 10:
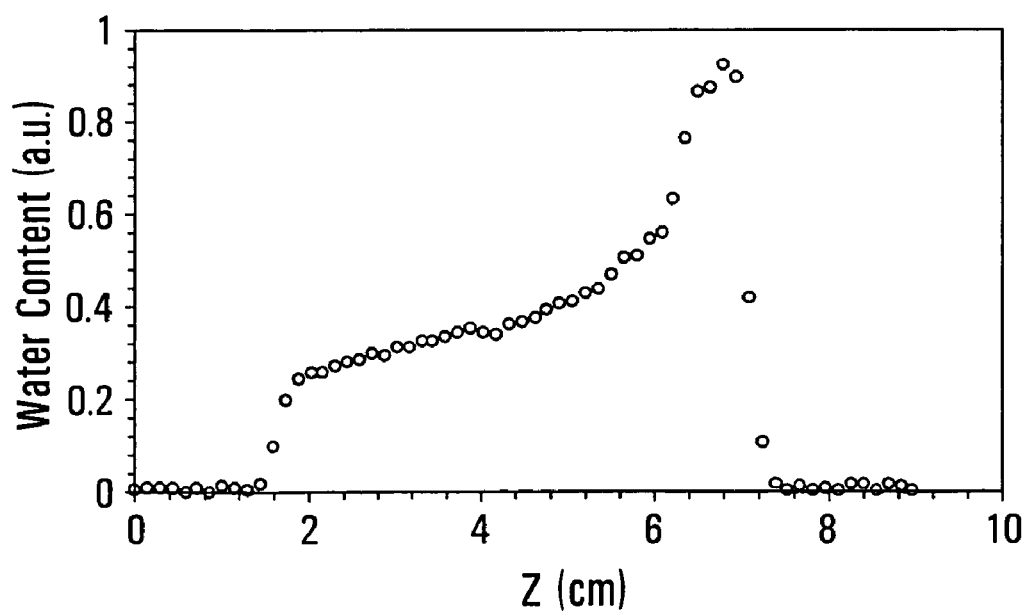
FIG. 10 shows a one dimensional water content distribution along the length of a Berea sandstone sample after centrifugation.
Figure 11:
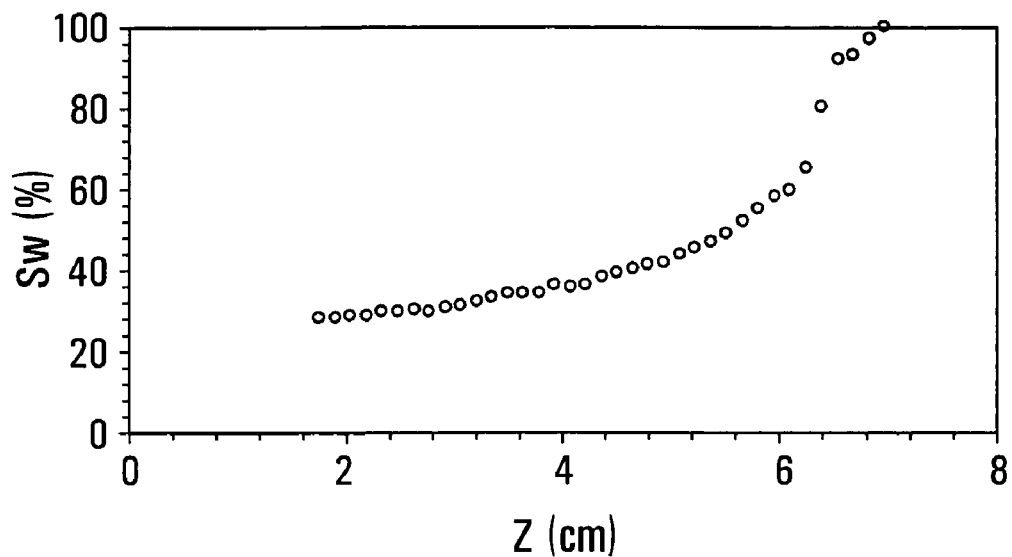
FIG. 11 shows a one dimensional saturation distribution along the length of a Berea sandstone sample after centrifugation.

FIGS. 9 and 10 show the 1D water content distribution along the length of the sample before and after centrifugation of the Berea sandstone core, respectively. The Berea sample was spun at a single speed of 1500 RPM for 2 hours. After centrifugation, the average water saturation ($S_w$) was 46.31% measured gravimetrically. After centrifugation, the water content gradient along the length of the core shows the effect of the centrifugation force distribution along the core. FIGS. 9 and 10 were calculated according to equation (25), yielding 1D water saturation distributions along the length of the Berea core, as shown in FIG. 11. The water saturation at the outlet surface is equal to 1, which shows that the outlet boundary condition is satisfied. Thus, MRI can be used to check the boundary condition for centrifugation experiments.

Figure 12:
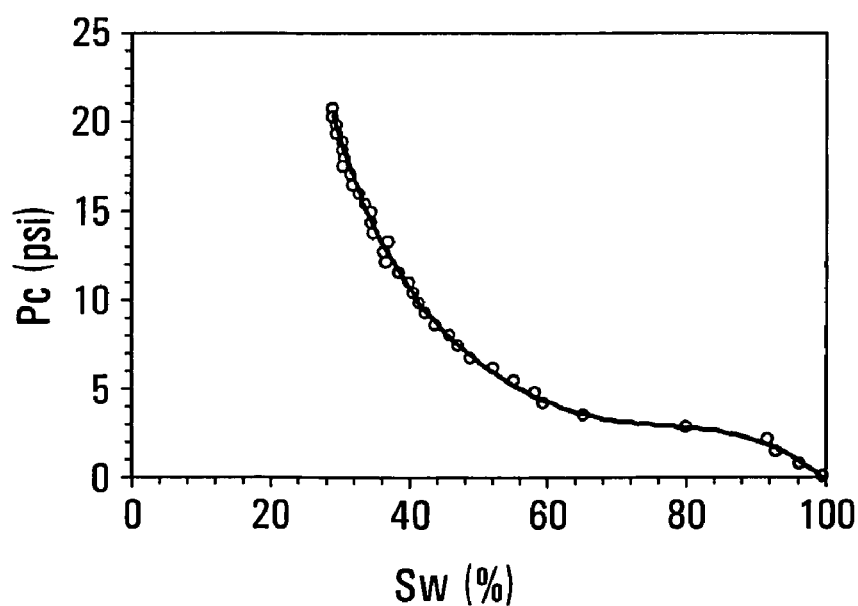
FIG. 12 shows an example of a capillary pressure curve of a Berea sandstone sample obtained by a single-speed centrifuge and MRI.

The capillary pressure distribution along the length of the core can be calculated through equation (11). Thus, the relationship between capillary pressure and the corresponding water saturation can be established very straightforwardly. The capillary pressure curve is obtained as, for example, shown in FIG. 12. In this example, the curve contains 37 data points. It may be smoothed through fitting to a polynomial for further data processing.

Figure 13:
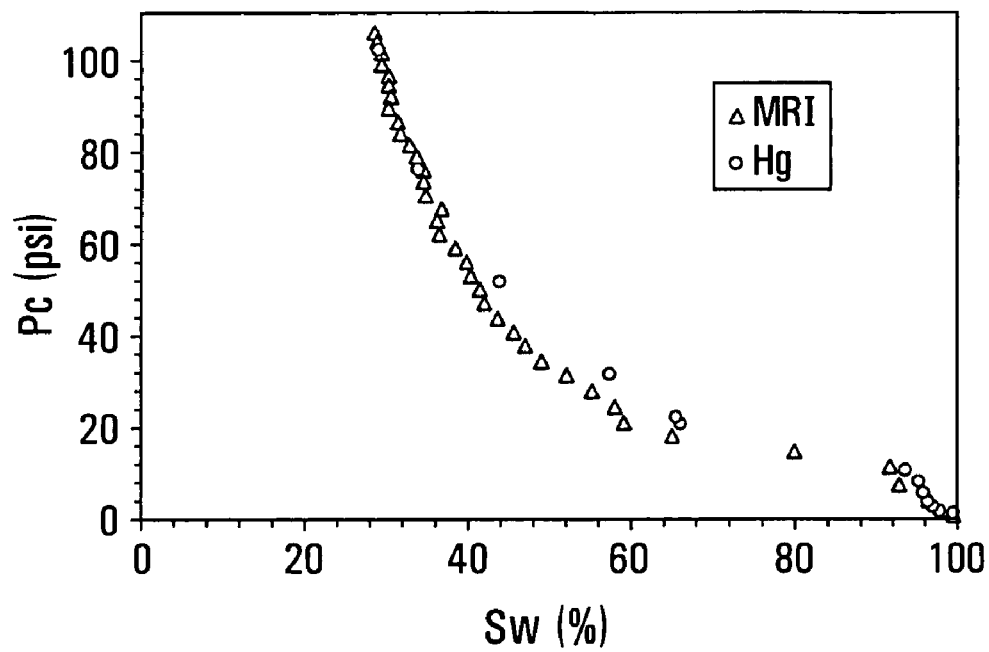
FIG. 13 shows a comparison of capillary pressure curves of a Berea sandstone sample obtained by a single-speed centrifuge and MRI, and by mercury intrusion.

The capillary pressure curve obtained with water and air can be converted to a capillary pressure curve under mercury intrusion. For a water and air system, σ=72 Mn/m and θ=0 degree; for mercury intrusion, σ=480 Mn/m and θ=140 degree. A comparison of the capillary pressure curves obtained by the new method and by mercury intrusion porosimetry are shown in FIG. 13, and the data indicates that the two methods are remarkably consistent.

Figure 14:
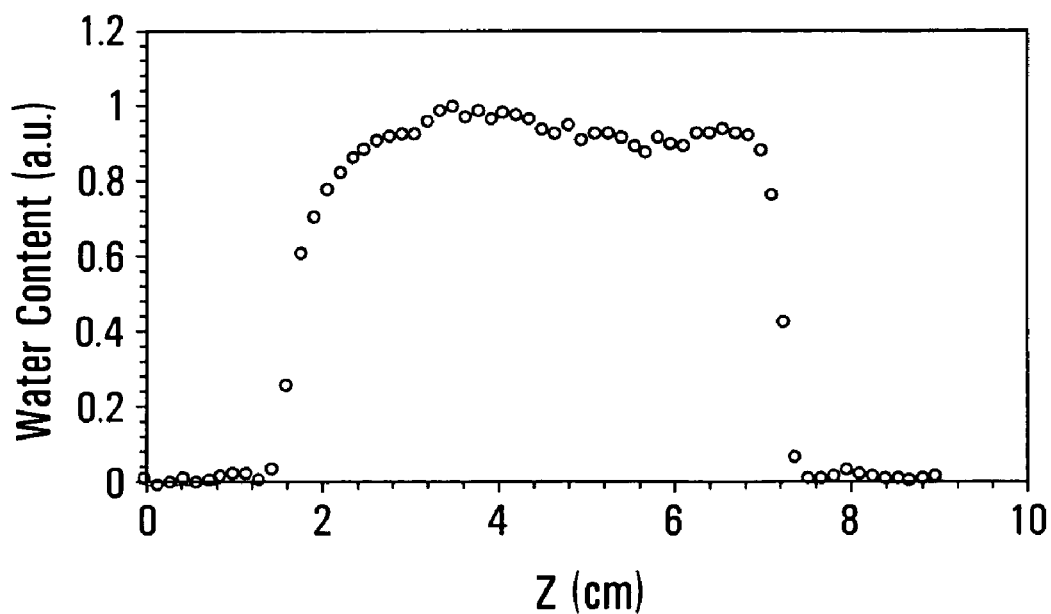
FIG. 14 shows a one dimensional water content distribution along the length of a Berea sandstone sample with 100% saturated state.
Figure 15:
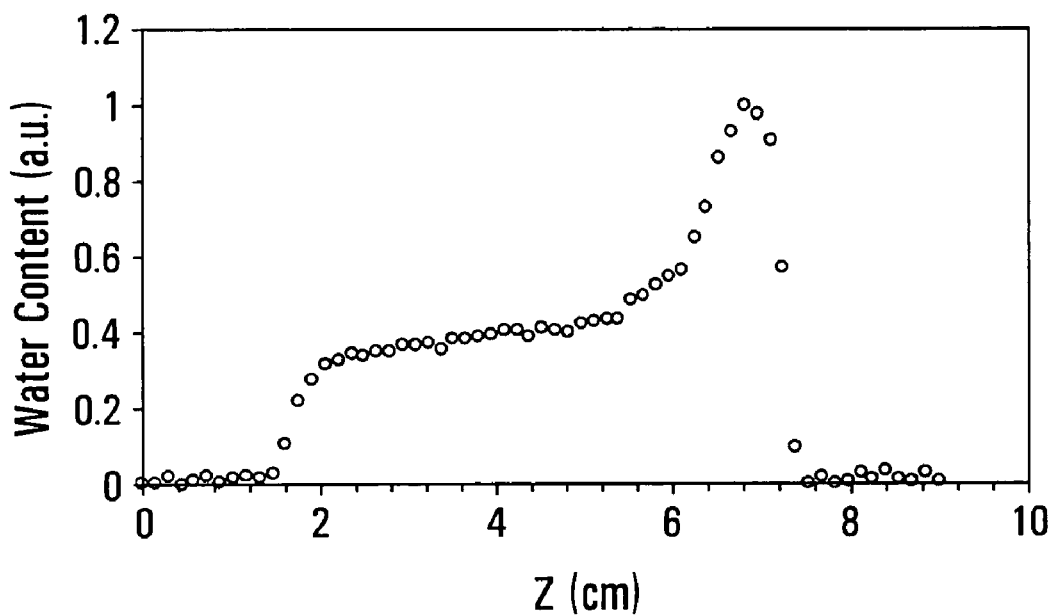
FIG. 15 shows a one dimensional water content distribution along the length of a sandstone sample (#125) after centrifugation.
Figure 16:
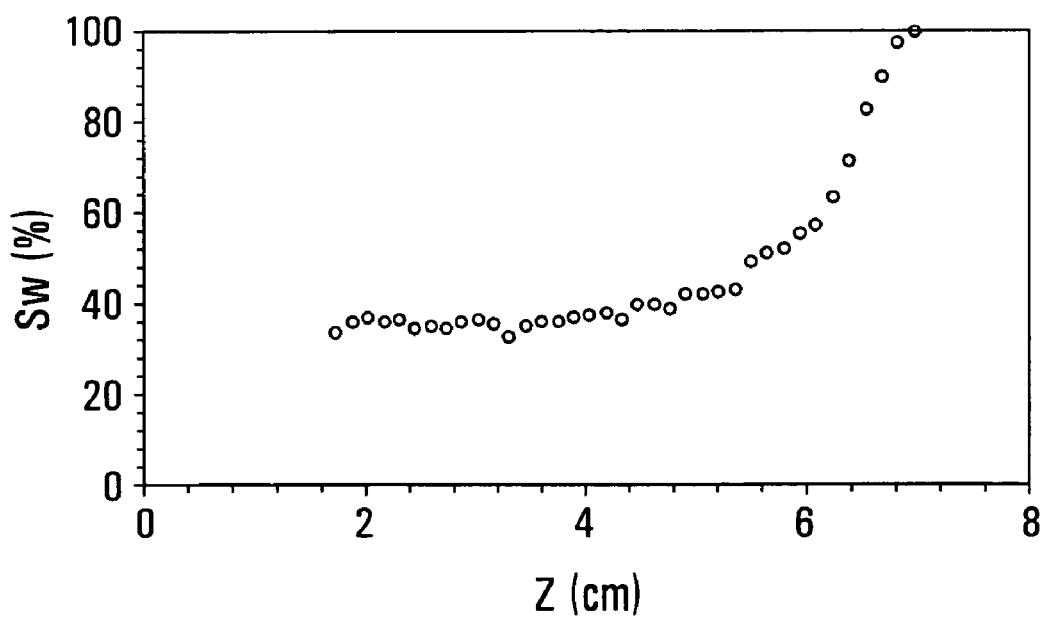
FIG. 16 shows a one dimensional saturation distribution along the length of the sandstone sample of FIG. 15.
Figure 17:
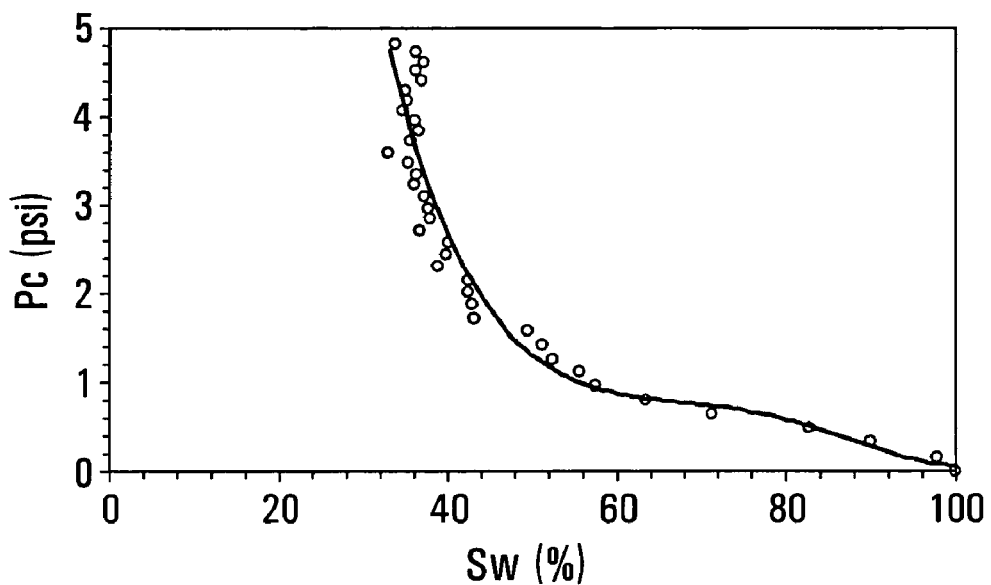
FIG. 17 shows a capillary pressure curve for the sandstone sample of FIGS. 15 and 16 obtained by a single speed centrifuge and MRI.

For the sandstone core #125, the water content distribution along the length of the sample before and after centrifugation is shown in FIGS. 14 and 15, respectively. During centrifugation, the sample was spun at a single speed of 750 RPM for 35 minutes. After centrifugation, the bulk water saturation (Sw) was 49.42% determined gravimetrically. The 1D water saturation distribution along the length of the core is depicted in FIG. 16. The water saturation at the outlet surface of the core is 1, indicating that the outlet boundary condition is maintained. The corresponding capillary pressure curve is illustrated in FIG. 17.

Figure 18:
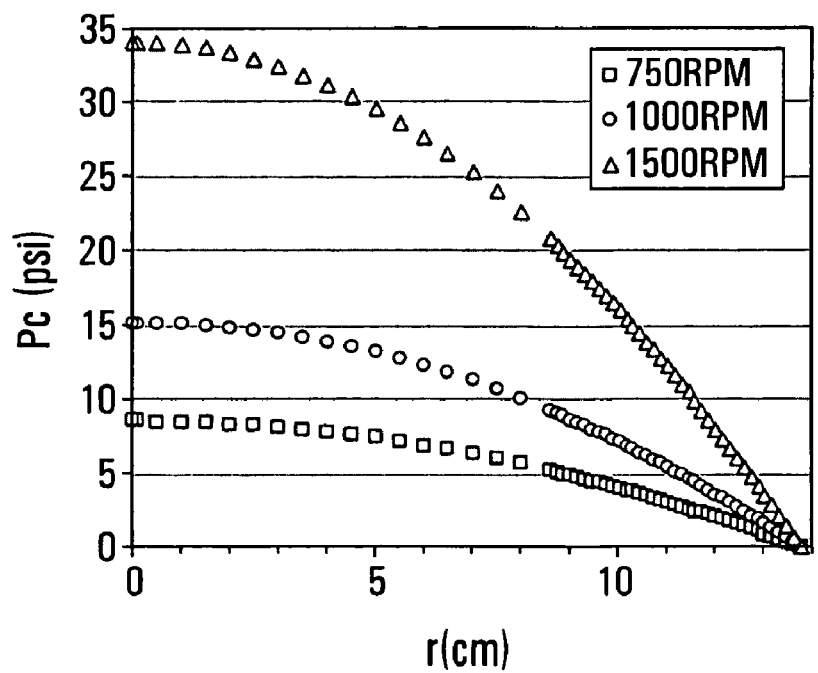
FIG. 18 shows three capillary pressure distributions along the length of a core corresponding to different rotational speeds.

FIG. 18 shows three capillary pressure ($P_c$) distributions along the length of the core corresponding to different rotational speeds of 750 RPM, 1000 RPM, and 1500 RPM. The centrifuge radius to the bottom of the core ($r_2$) was 13.8 cm. The capillary pressure ($P_c$) distribution was calculated according to Equation (11). There are two ways to increase the range of capillary pressure distribution, i.e., increase the length of the sample or increase the rotational speed. The proposed method employed a long sample and a single moderate rotational speed to create a large range of capillary pressure distribution and water saturation distributions.

The rotational speed is required to be sufficiently large to ensure that an irreducible water saturation condition is reached at the inner-surface of the core. An estimate of the capillary pressure for irreducible water may be obtained by the Leverett J function, as described in Leverett M. C., Trans. AIME, 142, 152 (1941). The selected speed will generally be dramatically less than the maximum speeds employed in the traditional measurement.

The gravity effect on the traditional centrifuge method has been discussed by Ruth and Chen in D. Ruth and Z. Chen, The Log Analyst 36, 21 (1995). When running the centrifuge, the direction of centrifugal acceleration, $a_c$, at any point r along the rational distance within the core plug is perpendicular to the rotational axis, the value of the centrifugal acceleration is $\omega^2 r$. However, gravity will result in an inclined acceleration field, and the capillary pressure inside the core plug is actually counterbalanced by this inclined acceleration, $a_{cg}$, which includes both centrifugation acceleration and gravity acceleration effects. The angle (φ) between $a_{cg}$ and $a_c$ is given by $\phi=\arctan(g/\omega^2 r)$. At low rotational speed during traditional centrifuge capillary pressure measurement, the effect of gravity on the centrifugal field can not be neglected.

In addition, the traditional centrifuge method is time consuming and special instrumentation is required for the experiment. These disadvantages can all be avoided through the new methodology.

The rock sample for centrifuge capillary pressure measurement is assumed to be homogeneous, MRI can be employed to check the inhomogeneity of core.

The capillary pressure curve, for the same sandstone reservoir core, is readily determined by plotting the saturation as a function of the capillary pressure, determined from Eq. 11, where both are known or determined functions of r. The MRI centrifuge results agree well with mercury intrusion porosimetry results.

Advantageously, in this methodology, minimal or no assumptions are required, unlike the traditional measurement. Note that the method allows the sample to be spun at a very moderate rate, for a reasonably short time, and that implicitly a check (through the MRI measurements) is available of the outlet boundary condition according to which $P_c(r_2)=0$; and the saturation $S(r_2)$ is unity (i.e. full).

The method allows a wide range of cores with a wide range of porosity and permeability to be tested, including challenging cores from marginal reservoirs. Samples may include water wet and oil wet samples. A sample diameter of 1 inch may be chosen in keeping with industry standard core diameters, or samples of any other diameters may be used.

A determination of optimum and realistic core rotation speeds, and core lengths, for a wide range of samples can be made.

A determination of the time to saturation equilibration can be made for a wide range of samples. Equilibration is faster for moderate centrifugation speeds and may be directly checked by MRI measurements. Also a determination of the maximum permissible measurement time interval after centrifugation can be made. Centrifugation creates a non-equilibrium fluid distribution which will change due to capillarity, diffusion and inlet/outlet drying once the sample is removed from the centrifuge. These effects will alter $S(r)$ but may be measured directly by MRI—as a function of time after centrifugation. The MR relaxation time behavior of a range of samples as a function of saturation may also be determined and that $T2^*$ is single exponential at low field with minimal variation with saturation, may be verified.

Irrespective of the detection strategy chosen, the image acquisition time may be optimized to permit rapid sample throughput and multiplexed sample analysis. Measurements may be performed rapidly with centrifugation times of under one hour, and with four (or any other number of) samples simultaneously. MRI detection times can be under 10 minutes each. MRI measurement times, in the simplest case, can be under one minute.

In embodiments of the invention, rotation speeds of under 2000 rpm would be sufficient for cores of 5 to 6 cm in length. Higher rotation speeds compensate for shorter sample length. The MRI measurements permit controlled measurements of $S(r)$.

Measurements can be performed on a high field (2.4 Tesla) magnet, or on a low field desktop magnet. Embodiments of the method may use $^1H$ MRI measurements, and/or may also employ RF probes for $^2D$ and $^{19}F$ experiments.

Embodiments of the apparatus may comprise a commercial desktop centrifuge adjacent to the low field MRI system. Sample holders which collect the expelled fluid at the outlet can be used, and/or sample holders which permit adding an additional fluid to the inlet end.

In one embodiment, measurement involves a side by side table top centrifuge and table top MRI instrument.

Figure 19A:
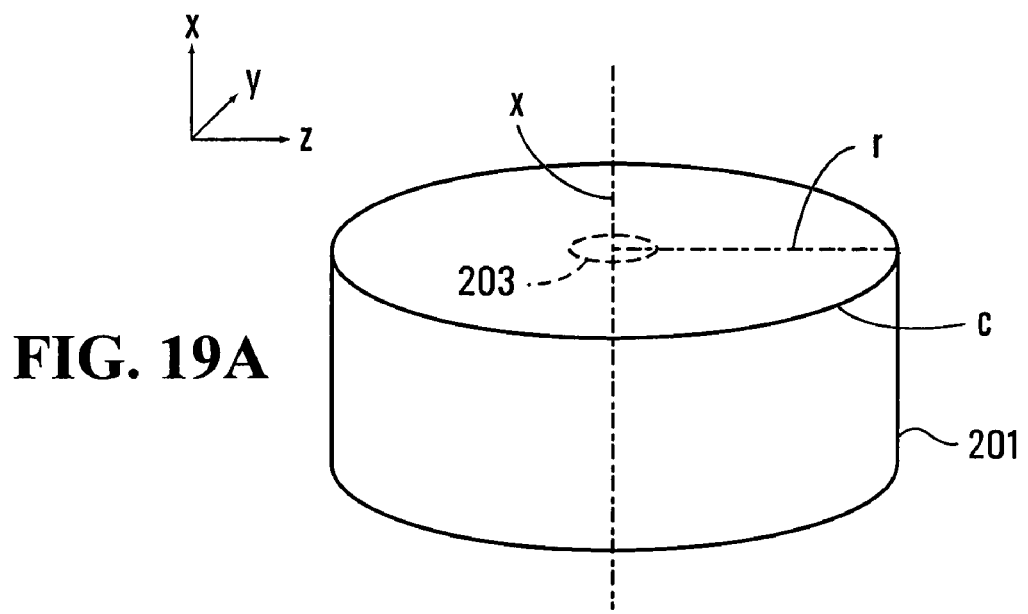
FIG. 19a shows a schematic diagram of a disk sample.

In other embodiments of the present invention, the sample holder may be adapted for mounting the sample such that a portion of the sample extends either side of the rotational axis. In one embodiment, the sample may comprise a disk and the sample holder is adapted to hold the disk so that the centre of the disk is coaxial with the rotational axis of the centrifuge. FIG. 19a shows a schematic diagram of a disk-shaped sample 201 whose fluid distribution as a function of capillary pressure is to be measured. Initially, the disk is saturated with fluid and the fluid content is measured along a radius, r, for example from the centre, x, of the disk to its circumferential edge, c, or along any portion of the radius. The fluid distribution may be measured using MRI techniques, described above.

In one embodiment, the disk sample may have an optional hole or aperture (e.g. aperture 203) formed in the centre of the disk and which extends partially or completely through the disk between its opposed flat faces. This may assist in enabling the disk to draw in fluid during centrifugation or otherwise. In this case the inner wall of the aperture effectively becomes the 'inlet face' of the sample, the 'outlet face' being the circumferential surface.

Figure 19B:
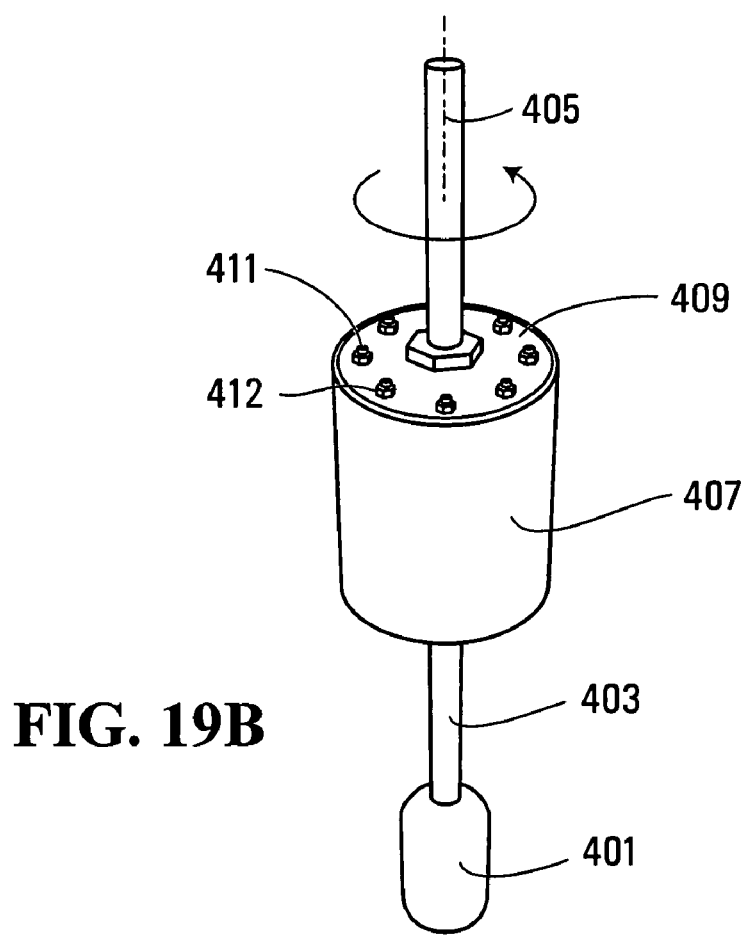
FIG. 19b shows an embodiment of a sample holder and centrifuge according to an embodiment of the present invention.

The same disk is then mounted in a centrifuge sample holder, an example of which is shown in FIG. 19b. Referring to FIG. 19b, the centrifuge comprises a motor 401, a drive shaft 403 which rotates about a rotational axis 405, a sample disk holder 407, which in this embodiment is cylindrical, (but could be any other shape) a removable end closure 409 at one end of the disk holder and fastening means 411, for example an arrangement of bolts and/or nuts (or other fastening mechanism), for securing the sample in the holder.

Using a sample which extends across the axis of rotation, such as a disk-shaped sample allows the rotary elements of the centrifuge, such as the sample holder to be more compact. As data points can be measured along a number of different radii of the sample, a better signal-to-noise ratio can be obtained. Furthermore, with a circular disk, the value of $r_2$ for the outlet boundary is constant and precise, in comparison to a longitudinal sample having a flat outlet end, where $r_2$ is an approximation. Accordingly, using a circular disk eliminates these 'radial' effects, thereby increasing the accuracy of the measurement. In addition, as the rotary components of the centrifuge can be radially more compact, and the sample lighter, the moment of inertia is reduced, causing less vibration and frictional heating, and also enabling the sample to be spun at higher speeds. In some embodiments, the diameter of the disk may be 10 to 12 cm, whereas the rotor and sample holder assembly of a conventional centrifuge typically has a diameter of 30 to 50 cm.

In practice, the sample is treated, e.g. saturated with a fluid such as water before being mounted in the sample holder and is then spun in the centrifuge. Saturation may be achieved by immersing the sample in fluid (liquid) and applying a negative pressure e.g. vacuum to the liquid (surface) to draw the fluid into the sample and displace air or other fluid from the sample.

In embodiments of the present invention, the sample holder may be mounted either externally of an MRI system or within an MRI system. Advantageously, this latter arrangement eliminates the need for removing the sample from the centrifuge and mounting a sample in the MRI instrument, and therefore simplifies the measurement procedure and saves time.

Figure 20:
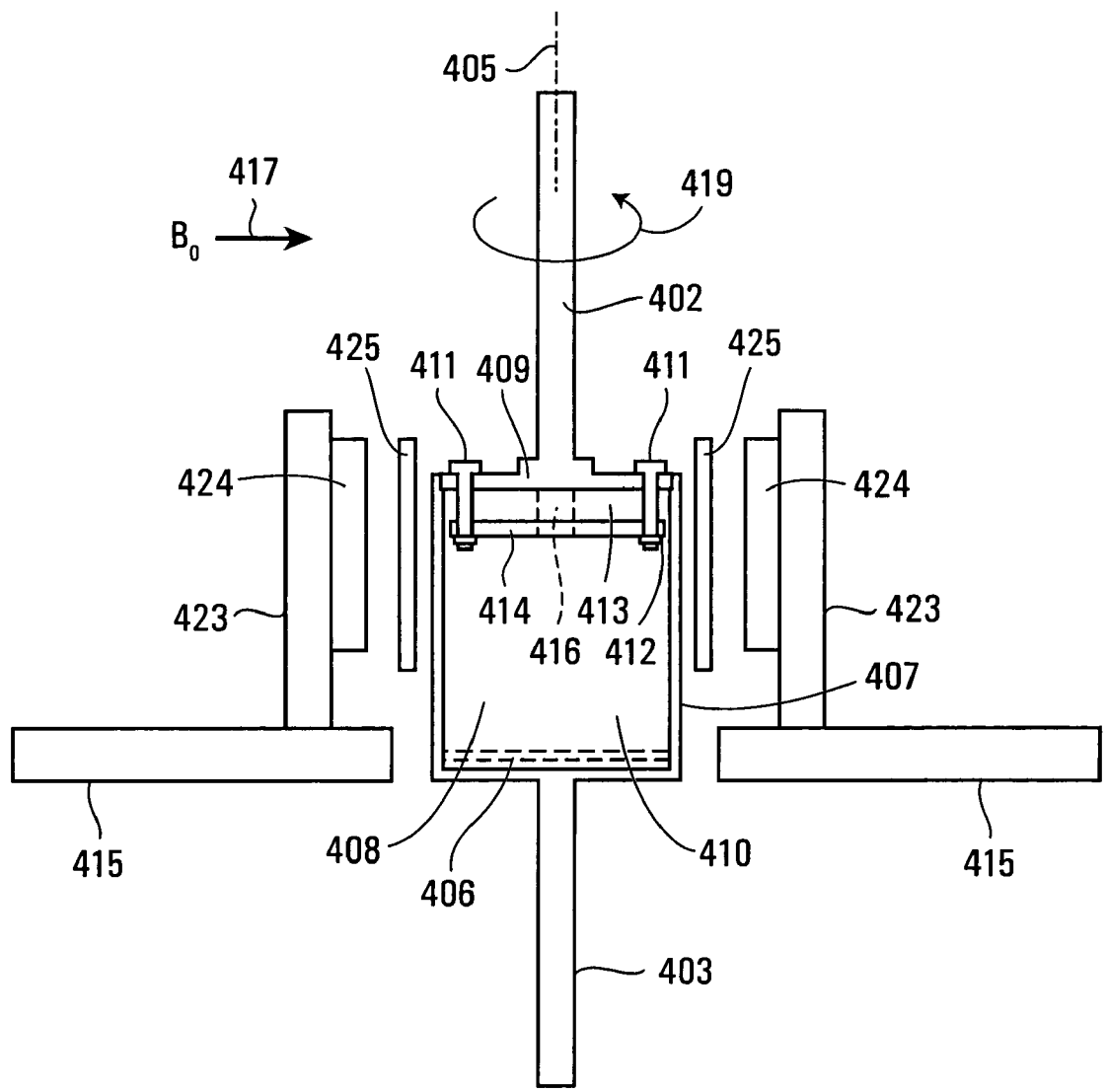
FIG. 20 shows a cross-sectional view of the sample holder shown in FIG. 19b incorporated within an MRI apparatus according to an embodiment of the present invention.

An example of an arrangement in which a sample holder is mounted within an MRI system is shown in FIG. 20. In FIG. 20, the sample holder is the same as that shown in FIG. 19b, and is shown in cross-section. The MRI system comprises a permanent magnet 423, a gradient set 424 and an RF coil 425. The sample holder 407 has upper and lower shafts 402, 403 extending therefrom and comprises a chamber 408, the lower portion 410 of which serves as a liquid collector for collecting liquid 406 expelled from the sample during centrifugation. The sample holder has an upper sample disk holder plate and closure 409 (which is coupled to the upper shaft 402) and a lower sample disk holder plate 413, between which is mounted a sample disk 413. Advantageously, this configuration allows the sample to be held in place by clamping which obviates the need to make holes in the sample or otherwise modify the sample for fastening to the holder.

An aperture 416 may be formed in a central region of the lower disk 414 to assist in allowing the disk to draw in fluid (e.g. air, water or oil) to replace fluid expelled from the sample. The aperture may permit fluid communication with an aperture (e.g. 203 in FIG. 19A) if one is provided. The sample disk may have a typical diameter of 10 to 12 centimetres and a thickness of about 1 centimetre, for example, although any other suitable dimensions may be used. The sample is clamped between the upper and lower plates by means of bolts and nuts 411, 412 or other suitable means. A platform 415 is provided to support the permanent magnet. In this embodiment, the lower portion of the sample holder extends below the bottom of the RF coil 425 so that expelled liquid from the sample disk resides outside the RF coil.

An arrow 417 shows the direction of the magnetic field Bo. A circular arrow 419 shows the spin direction of the rock disk holder, although in other embodiments the spin direction may be reversed. The amount of liquid within the spinning rock disk can be monitored by NMR bulk measurements, such as free induction decay and CPMG (Carr-Purcell-Meiboom-Gill). After a hydrostatic equilibrium state is reached, the spin is ceased, and 2D MRI imaging is carried out along the YZ plane (with reference to FIG. 19A) to obtain the 2D liquid distribution within the rock disk. This distribution is analyzed to determine S(r), the saturation radially. It is to be noted that the components of the apparatus shown in FIG. 20 are not necessarily to scale, and the magnet is rotated 90° from FIG. 5.

Examples of Capillary Pressure Curve Measurements Using a Disk Sample

An example of a procedure for measuring the primary drainage capillary pressure curve of a rock disk sample in a rock disk centrifuge is as follows.

1. The rock disk sample is dried at an elevated temperature of for example 80° C., until a constant weight is reached, and the weight of the dried sample is determined.

2. The rock disk sample is kept under vacuum conditions for a period of time, for example 24 hours, and then saturated with distilled water ($H_2O$) under vacuum conditions, until no bubbles are released from the rock disk sample. The weight of the saturated sample is then determined. The difference between the weight of the saturated sample and the dried weight provides the total weight and total volume of water in the saturated sample.

3. A proton ($H^1$) Spiral SPRITE MRI measurement is carried out on the rock sample which may be wrapped with a fluid impervious tape such as Teflon, to decrease the evaporation of water from the sample during MRI measurements. A water distribution along the radii of the sample is obtained and normalized with total volume of water in the rock disk sample.

4. The rock disk sample is placed in a rock disk sample holder (which may be non-magnetic) for centrifugation at a selected speed for a predetermined time. In a specific example, the sample was spun at 1920 RPM for one hour for the primary drainage capillary pressure curve measurement.

5. The MRI measurement of step 3 is then repeated to provide the water saturation distribution along the radii of the rock disk sample after centrifugation. The total volume of water in the rock disk sample after centrifugation is also determined.

6. A water distribution along the radii of the sample is obtained and normalized with the total volume of water in the rock disk sample after centrifugation.

7. The water saturation ($S_w$) distribution along the radii of the rock disk sample after centrifugation was determined from the volume normalized water distribution after centrifugation divided by the volume normalized water distribution before centrifugation. The capillary pressure curve is determined with saturation distribution and capillary pressure distributions along the radii of the rock disk sample.

EXPERIMENTAL RESULTS

In one specific experiment, a Berea sandstone disk was used having a diameter of 4 inches and a thickness of half an inch. The capillary pressure measurements were conducted according to the experimental procedure described above.

Centrifugation of the sample was performed using a spinning rock disk non-magnetic sample holder and centrifuge as shown in FIGS. 19 and 20. The sample was spun at a speed of 1920 RPM for one hour. The temperature of the centrifuge was controlled and maintained at a temperature of 4° C. to reduce or avoid evaporation of water within the rock disk sample during the centrifugation process.

The water distribution was determined using a SPRITE MRI measurement performed in a 2.4 Tesla horizontal bore superconducting magnet available from Nalorac Cryogenics Inc., Martinez, Calif., with an Apollo console from Tecmag Inc., Houston, Tex. A 14 cm inner diameter eight-rung quadrature birdcage probe, from Morris Instruments, Ottawa, ON, was employed. As indicated above, the core samples were wrapped with Teflon tape to decrease the evaporation of water from the samples during MRI measurements.

A two-dimensional image of the sample in the y, z, plane was measured br a predetermined value of x, the position of the plane along the sample axis. The two-dimensional images before and after centrifugation were obtained using a Spiral SPRITE MRI technique, which involves increasing the x and y gradients in a progressive manner which avoids both field gradients having a maximum value at the same time to increase the signal-to-noise ratio of the measurement. In one example of the measuring scheme, the phase encoding time was 50 microseconds, the flip angle $\alpha$ was 6 degrees, the field of view was 17 cm and the image matrix size was 64*64 points. For each of 64 points, 64 signal averages were acquired and the total acquisition time was 3 minutes. It is to be noted that more data points along the length of the core can easily be obtained by increasing the image matrix size and/or decreasing the field of view of the image, which results in more data points on the capillary pressure curve.

Figure 21:
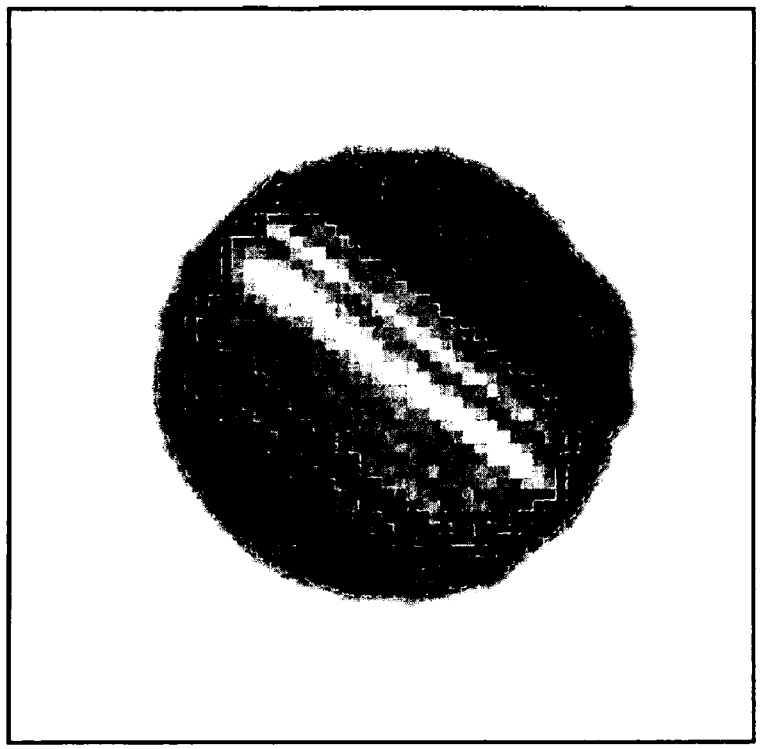
FIG. 21 shows a two-dimensional MRI image for a fully water saturated rock disk sample using a spiral SPRITE MRI technique.
Figure 22:
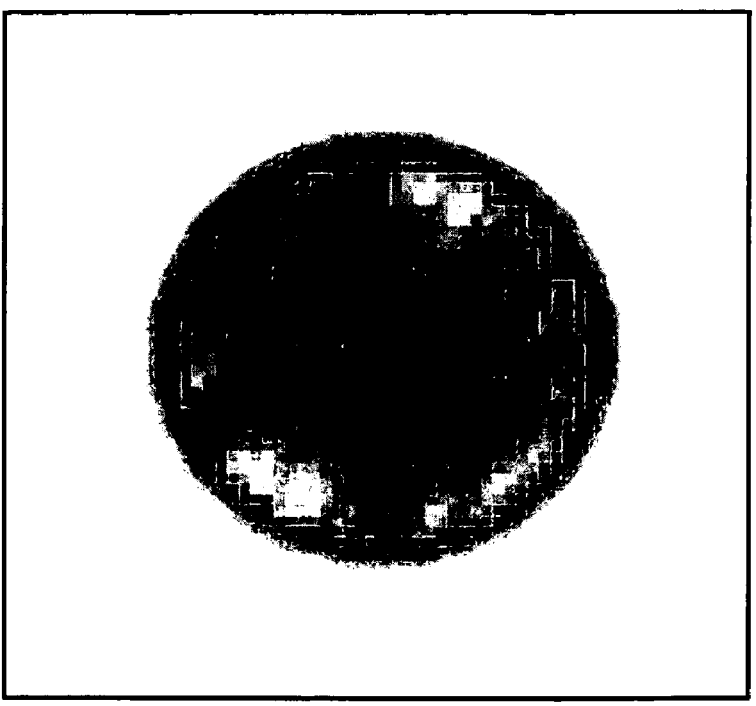
FIG. 22 shows a two-dimensional MRI image for the rock disk sample of FIG. 19A after centrifugation at 1920 RPM in air.

FIG. 21 shows a two-dimensional image of a fully water saturated rock disk sample using Spiral SPRITE MRI measurement. FIG. 22 shows a two-dimensional image of the water saturated rock disk sample after centrifugation at a speed of 1920 RPM in air, again using Spiral SPRITE MRI. After centrifugation, the average water distribution was 44%.

Figure 23:
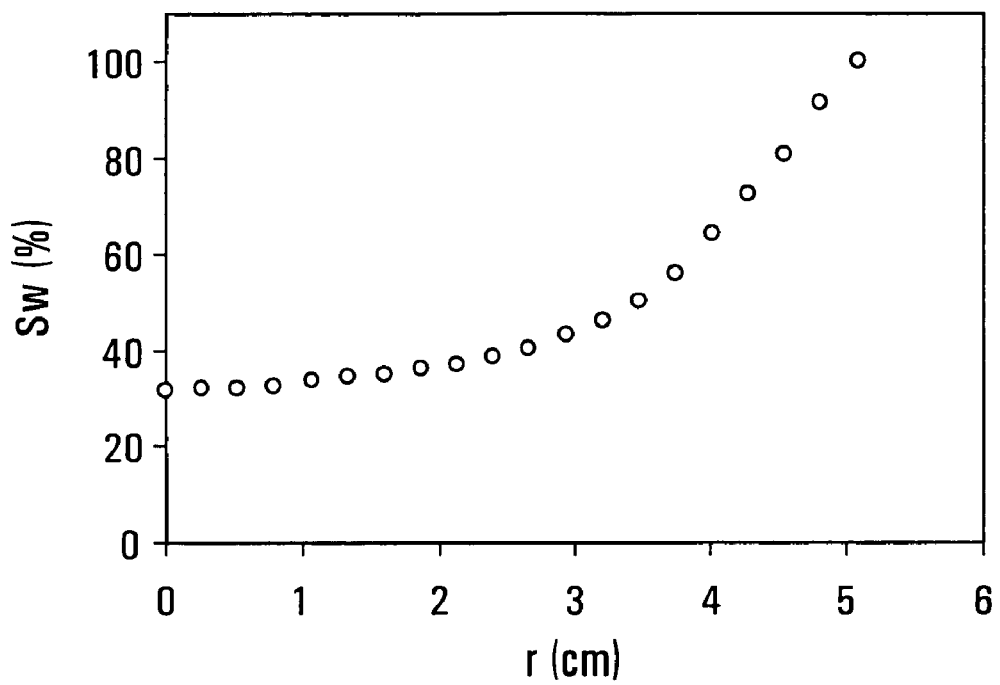
FIG. 23 shows a graph of the water saturation distribution along the radii of the sample disk core after centrifugation at 1920 RPM in air.

FIG. 23 shows a graph of the water saturation distribution along the radii (r) of the rock disk.

Figure 24:
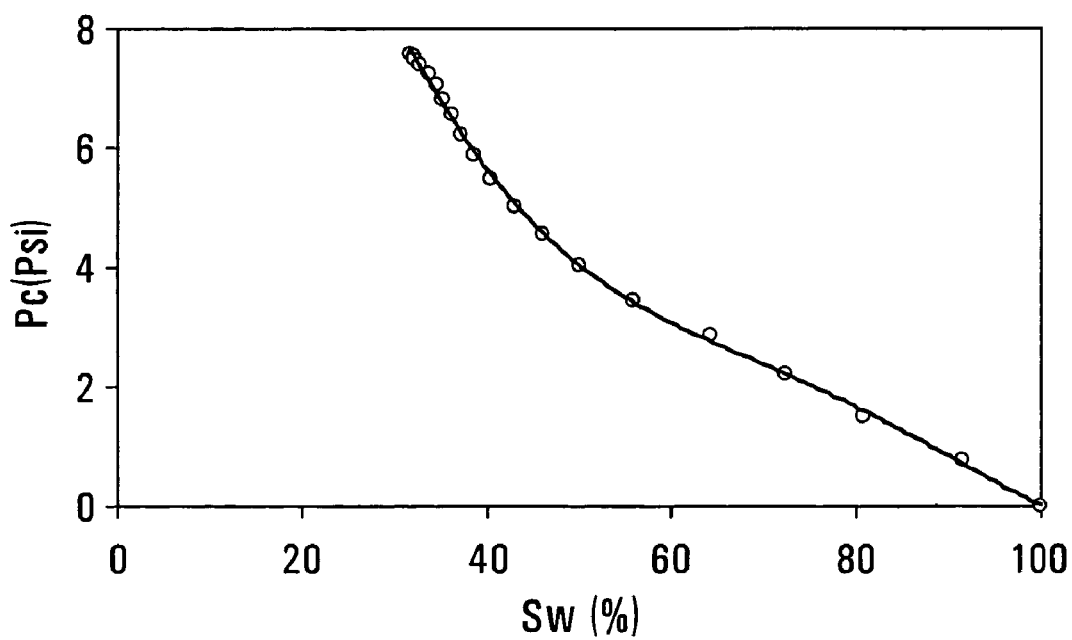
FIG. 24 shows a capillary pressure curve derived from the data of FIG. 23 for the disk sample obtained by single speed centrifuge and SPRITE MRI.

The relationship between capillary pressure and the corresponding water saturation can be determined very straightforwardly from the data shown in FIG. 23 and the corresponding capillary pressure curve is shown in FIG. 24.

The Spiral SPRITE MRI methodology is described in Halse, M., Goodyear, D. J., MacMillan, B., Szomolanyi, P., Matheson, D. and Balcom, B. J., Journal of Magnetic Resonance 165, 219 (2003) and Chen Q., Halse M. and Balcom B. J., Magnetic Resonance Imaging, 23, 263 (2005), the entire content of which are incorporated by reference. In this imaging technique, the 2D scanning gradients (e.g. $G_x$ and $G_y$) are ramped sinusoidally yielding a spiral k-space trajectory. This technique helps reduce the occurrence of simultaneously high values of the gradients, thereby improving the signal-to-noise ratio of the measurement. In other embodiments, any other imaging technique may be used (either 1D, 2D or 3D).

The conventional measurement is not used to full potential because of concerns over its validity, its high unit measurement cost, and the long measurement time. The present methodology greatly improves upon indirect measurements of pore fluid reservoir interactions, such as core flooding and mercury intrusion porosimetry.

The measurement methods of the present embodiments can be faster, cheaper and better than traditional centrifuge measurements. The measurement technique is particularly suitable in the current exploration climate, with a renewed focus on difficult or marginal reservoirs, in difficult and expensive locales.

Embodiments, where centrifugation is performed within the MRI magnet, may involve spinning a disk like (or other shaped) sample, whose diameter may be in the range of 2 to 4 inches or any other value, in a turntable-like fashion. In this case the centrifugal force varies radially, and either a 1D or 2D MRI analysis of the capillary pressure and fluid saturation distribution can be performed. A 2D MRI analysis would be straight forward.

A low field permanent magnet for MRI may be used. Field drift of the magnet may not be a significant problem and in an end use instrument the problem is easy to correct through active temperature control. The desktop centrifuge may be a completely standard turn-key instrument associated with a 2D disk-like centrifugation within the magnet. The entire centrifuge apparatus is preferably both non-magnetic and non-conducting with the motor, driving the axial spin, removed from the magnet by at least one meter.

A new method to measure the capillary pressure curve using a single speed centrifuge experiment and magnetic resonance imaging has been described. The advantages of the method for determining capillary pressure curve are vastly increased speed of measurement, dramatically increased precision, and decreased cost through a more rapid process with an inexpensive desktop centrifuge and desktop MRI. The new method may use a long core to directly measure a large range of saturation distribution along the length of the core at a single moderate speed of centrifuge, without any assumptions. The capillary pressure curve can be obtained straightforwardly with 40 to 50 spatial data points, for example. The duration of the experiment is reduced by a factor of 15 compared to the traditional method. Since only one moderate centrifuge speed is employed, the boundary conditions can be maintained and the centrifuge speed selected to be sufficient so that the effect of gravity is very small.

The methodology of capillary pressure curve measurement using a single-speed centrifuge with air displacing water may be extended to a water/oil system, in which water displaces oil or vice versa, for primary drainage, imbibition, and secondary drainage capillary pressure curve measurements.

Embodiments of the method may be used to perform drainage capillary pressure curve and imbibition capillary pressure curve measurements where oil and water phase displacement occurs during centrifugation. The MRI analysis allows oil and water phases to be distinguished. This may be done at least four different ways, (1) water saturation determination with $D_2O$ ($^2D$ MR), (2) oil saturation determination with a fluorinated oil ($^{19}F$ MR), (3) discrimination of 1H containing oil and water by $T_2$ relaxation time analysis combined with MRI, and (4) addition of either oil or water soluble paramagnetic contrast agents to eliminate signal from either soluble phase. All four approaches are compatible with MRI.

For a water/oil system, the $1^{st}$ drainage, imbibition, and $2^{nd}$ drainage capillary pressure curves can be obtained by centrifuge and MRI through the following three steps.

(1) A reservoir rock core (typical length 5-8 cm), is saturated with water under vacuum conditions. The core is positioned in the centrifuge core holder which is oil filled, a moderate rotation speed is selected to ensure that the irreducible water saturation can be reached at the inlet face of the core. This moderate rotation speed may be estimated by the Leverett J function, as described above.

After the hydrodynamic equilibrium state is reached, the rotation is ceased. The rock core is taken out of the holder and sealed with the Teflon tape. A 1D MRI image is taken along the length of the rock core to determine the water saturation distribution (S(r)). Interpretation of S(r) yields the $1^{st}$ drainage capillary pressure curve.

(2) The centrifuge core holder is filled with water, and the core is returned to the core holder with an inverted direction. The sample is rotated in the centrifuge with a moderate speed until the hydrodynamic equilibrium state is reached again. A similar process to procedure (1) is performed to obtain the water saturation distribution (S(r)) and the imbibition capillary pressure curve determined.

(3) The centrifuge core holder is filled with water once more, and the core is returned to the core holder with an inverted direction. The sample is rotated in the centrifuge with the moderate speed until hydrodynamic equilibrium state is reached again. A similar process to procedure (1) is performed to obtain the saturation distribution (S(r)) and the $2^{nd}$ drainage capillary pressure curve determined.

In order to measure drainage and imbibition capillary pressure curves where oil and water phase displacement occurs during centrifugation by MRI, it is necessary that the MRI measurements distinguish between oil and water phases, and this may be done at least four different ways as indicated above.

In some embodiments of the method, any one or more of primary drainage, imbibition and secondary drainage measurements may be made using $D_2O$ (heavy water) and oil. Advantageously, a proton ($H^1$) resonance frequency is chosen so that the MRI measurements do not contain a $D_2O$ signal. In this case, MRI measurements on a sample containing both oil and $D_2O$ will yield the oil distribution only. (Essentially, the MRI measurements are sensitive to the hydrogen in oil, but not to the deuterium in heavy water.) The corresponding water distribution in the sample can be deduced by subtracting the measured oil distribution from a measured total volume of fluid within the sample. Examples of methods for measuring primary drainage, imbibition and secondary drainage capillary pressure curves or capillary pressure scanning curves are described in more detail below. Specifically, embodiments of the method may comprise the following steps.

1. The cylindrical core sample is dried at an elevated temperature of, for example 80° C., until a constant weight is reached, and the weight of the dried sample is determined.

2. The core sample is kept under vacuum conditions for a predetermined period of time, for example 24 hours, and thereafter, the sample is saturated with distilled water (H$_2$O) under vacuum conditions until no bubbles are released from the core, and the weight of the saturated sample is determined.

3. The quantity (e.g. weight and total volume) of water drawn into the sample is determined by subtracting the weight of the saturated sample from the weight of the dried sample.

4. The sample is wrapped in a fluid impervious tape (e.g. Teflon tape) to decrease evaporation of liquid, and an MRI measurement is carried out on the sample. The MRI measurement may for example comprise a proton (H$^1$) double half k-space SPRITE MRI measurement. The measurement provides a water distribution along the length of the saturated sample. The saturated water distribution is then normalized with the total volume of water in the core sample, as determined in step 3.

5. Distilled water is removed from the sample, and the sample is saturated with heavy water (D$_2$O) instead. This may be achieved by repeating steps 1 and 2, where in step 2, the sample is saturated with D$_2$O instead of H$_2$O. The quantity (e.g. weight and volume) of D$_2$O present in the saturated sample is determined.

6. The saturated core sample is placed in an oil filled sample holder of a centrifuge for centrifugation to condition the sample for a primary drainage capillary pressure curve measurement. The sample is subjected to centrifugation at a predetermined speed for a predetermined length of time which is sufficient for the distribution of oil and D$_2$O in the sample to reach equilibrium. Any suitable speed may be selected. The time to reach equilibrium depends on the sample and may be estimated, (e.g. from known or measured parameters of the sample such as porosity) or MRI measurements of the fluid distribution may be made at intervals of time during the centrifugation process and the equilibrium condition measured. In one specific example, the centrifugation speed is 3000 RPM and the duration is 24 hours.

7. After centrifugation, the core sample is removed from the centrifuge and its weight determined. The quantity of oil drawn into the sample can be determined from the weight of the oil/D$_2$O saturated sample, and the determined pore volume of the sample.

8. The sample is wrapped with a fluid impervious tape (e.g. Teflon) to decrease the evaporation of liquid within the core sample during MRI measurements, and an MRI measurement, for example proton double half k-space SPRITE MRI, is made on the sample. The MRI measurements yield an oil distribution along the length of the sample, and the oil distribution is normalized with total volume of oil in the sample, as determined in step 7.

9. The D$_2$O distribution along the length of the sample is obtained by subtracting the volume normalized oil distribution along the length of the sample, found in step 8 from the volume normalized water distribution found in step 3.

Figure 25:
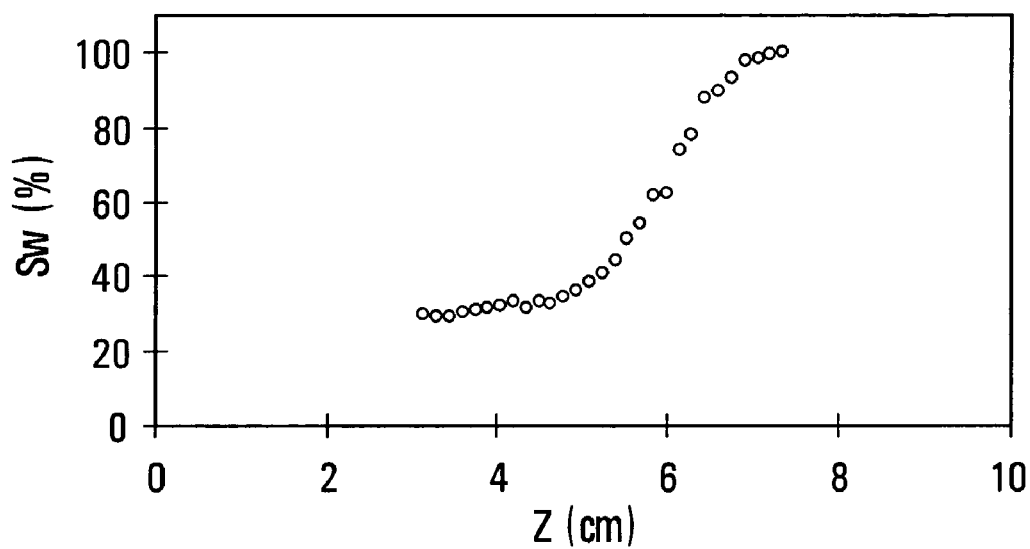
FIG. 25 shows a graph of the water saturation distribution along the length (z) of a core #126 after centrifugation at 3000 RPM in oil for 24 hours for a primary drainage capillary pressure measurement.

10. The water saturation (S$_w$) distribution along the length of the core sample (after centrifugation) is determined from the volume normalized D$_2$O distribution after centrifugation (found in step 9) divided by the volume normalized H$_2$O distribution before centrifugation (found in step 3). An example is shown in FIG. 25. The capillary pressure curve for primary drainage is determined from the saturation and capillary pressure distributions along the length of the sample.

11. To prepare the sample for an imbibition capillary pressure curve measurement, the sample is placed in the oil filled sample holder of the centrifuge in the reverse direction, i.e. flipped so that the inlet face becomes the outlet face and vice versa, and the core sample is spun for a period of time and then stopped. The sample may be flipped and spun again several times to reach a relatively uniform irreducible water (D$_2$O) saturation (S$_{wi}$) distribution along the length of the core sample. The sample will also contain a relatively uniform oil saturation.

12. The core sample, which now contains oil and an irreducible D$_2$O saturation distribution along its length, is placed in a centrifuge sample holder containing D$_2$O, for centrifugation for the imbibition capillary pressure curve measurement. (For consistency, the sample may be placed in the same inlet/outlet face orientation as for the primary drainage measurements.) Centrifugation is carried out at a predetermined speed for a length of time that is sufficient for the fluid distribution to reach equilibrium. This time may be estimated and/or measured, as indicated above. In one example, centrifugation is performed at 3000 RPM, and a time period of 48 hours was considered sufficient to reach equilibrium.

13. Steps 7-10 are then repeated. Thus, the core sample is removed from the centrifuge after centrifugation and its weight is determined. An MRI measurement is carried out on the sample, which may be wrapped in a fluid impervious tape to decrease evaporation of the liquid within the core during the measurement. An oil distribution along the length of the sample is obtained and normalized with the total volume of oil in the sample.

Figure 26:
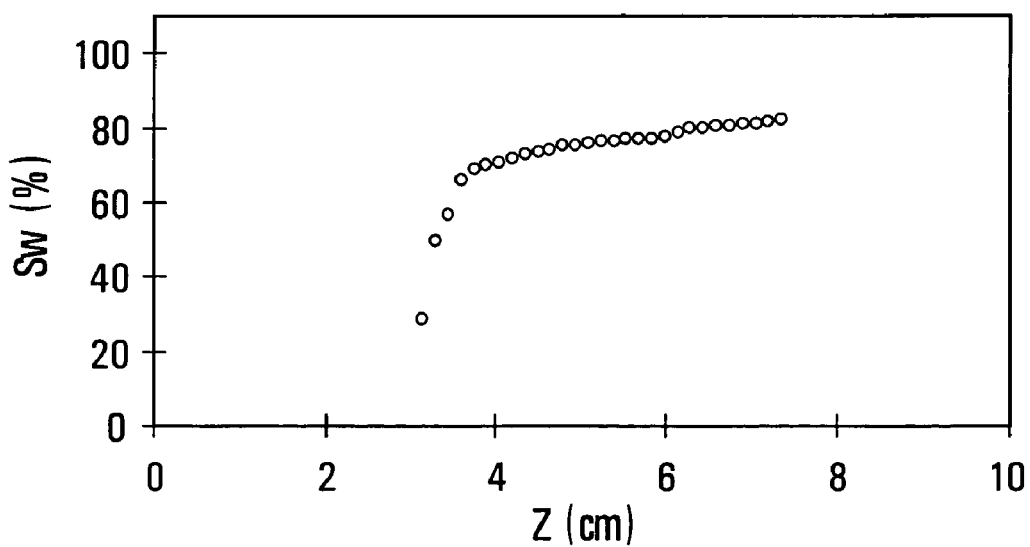
FIG. 26 shows the water saturation distribution along the length (z) of the core #126 after centrifugation at 3000 RPM in water for 48 hours for imbibition capillary pressure measurement.

The D$_2$O distribution along the length of the sample is obtained by subtracting the volume normalized oil distribution along the length of the sample from the volume normalized water distribution (found in step 3). The water saturation distribution along the length of the core sample is then determined by step 10. (An example of a measurement is shown in FIG. 26.) The capillary pressure curve for imbibition is determined from the saturation and capillary pressure distributions along the length of the core sample.

14. The core sample is then prepared for a measurement of the secondary drainage capillary pressure curve. The core sample is placed in a centrifuge sample holder containing D$_2$O in the reverse direction (i.e. flipped) from the previous centrifugation process and is spun in the centrifuge. The sample is flipped and spun again one or more times to take up as much D$_2$O as possible and to reach a relative uniform residual oil saturation (SOR) distribution along the length of the core sample.

15. The core sample is placed into a centrifuge sample holder containing oil for centrifugation at a predetermined speed for a period of time for the secondary drainage capillary curve measurement. The length of time of centrifugation should be sufficient for the fluid distribution in the sample to reach equilibrium. For example, the centrifugation process may be carried out a speed of 3000 RPM for a period of time of 48 hours.

Figure 27:
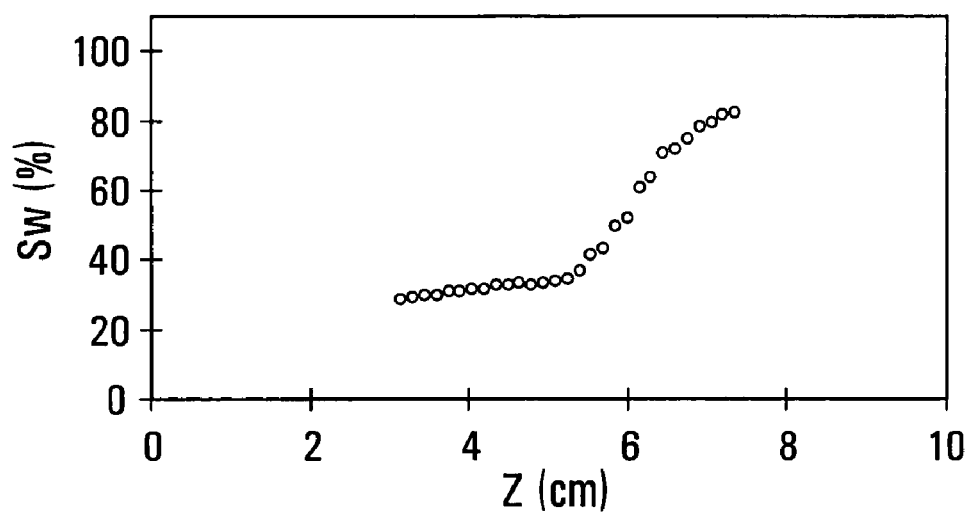
FIG. 27 shows the water saturation distribution along the length (z) of the core sample #126 after centrifugation at 3000 RPM in oil for 48 hours for secondary drainage capillary pressure measurement.

16. Steps 7-10 are repeated again. Thus, after centrifugation, the core sample is removed from the centrifuge and its weight is determined. An MRI measurement is performed on the sample, which may be wrapped in a fluid impervious tape to decrease evaporation of liquid within the core during the MRI measurements. An oil distribution along the length of the sample is obtained and normalized with total volume of oil in the sample. The $D_2O$ distribution along the length of the sample is obtained by subtracting the volume normalized oil distribution along the sample from the volume normalized water distribution (found in step 3). The water saturation distribution along the length of the core sample is then obtained using the procedure of step 10. An example of a measurement is shown in FIG. 27. The secondary drainage capillary pressure curve is obtained from the saturation and capillary pressure distributions along the length of the core sample.

EXPERIMENTAL RESULTS

In an example of a specific measurement, a cylindrical sandstone sample #126 was employed. The dimensions of the sample core were measured to determine the bulk volume of the rock sample. The capillary pressure measurements were conducted for primary drainage, imbibition and secondary drainage according to the experimental procedures described above.

The centrifuge measurements were made using a table top centrifuge, specifically model Z513K available from Hermle Labortechnick, Germany. Each centrifuge measurement was carried out at a speed of 3000 RPM for 24 or 48 hours.

MRI measurements were made using a 0.2 Tesla permanent magnet with an Apollo console available from Tecmag Inc., Houston, Tex. A 3 cm inner diameter solenoid probe was used. The core sample was wrapped with Teflon tape to decrease the evaporation of a liquid from the sample during MRI measurements. The advantages of using a low-field MRI instrument are that (1) the instrument is cheap and (2) effective spin-spin relaxation time ($T_2^*$) is much longer than the phase encoding time ($t_p$) for SPRITE MRI, to ensure that a spin density image is obtained.

In the measurements, decane, which has a relatively high hydrogen content, was employed as the oil phase. Other types of oil may also be used, such as crude oil to simulate reservoir conditions. The fluid content profiles along the length of the core before and after centrifugation were obtained by one-dimensional centric scan SPRITE MRI, with a phase encoding time of 50 µs, a flip angle α of 6 degrees, with an image matrix size of 64 points. 16 signal averages were required for a total acquisition time of one minute. More data points along the length of the core can easily be obtained by increasing the image matrix size and/or decreasing the field of view of the image, which results in more data points on the capillary pressure curve.

Figure 28:
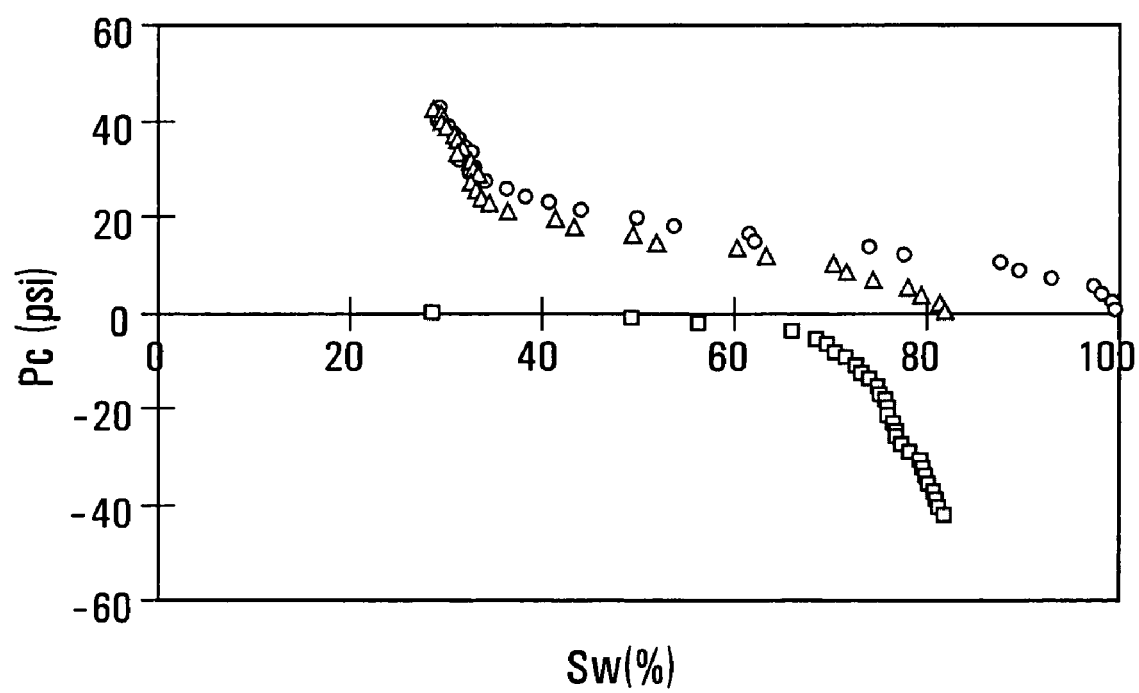
FIG. 28 shows a graph of the capillary pressure curves obtained by single speed (3000 RPM) centrifugation and sprite MRI for primary drainage (circle), imbibition (square) and secondary drainage (triangle).

FIGS. 25, 26 and 27 show the 1D water saturation distribution along the length of the core after primary drainage, imbibition and secondary drainage, respectively. In particular, FIG. 25 shows the water saturation distribution along the length (z) of a core #126 after centrifugation at 3000 RPM in oil for 24 hours for a primary drainage capillary pressure measurement. FIG. 26 shows the water saturation distribution along the length (z) of the sample after centrifugation at 3000 RPM in water for 48 hours for an imbibition capillary pressure measurement. FIG. 27 shows the water saturation distribution along the length (z) of the sample after centrifugation at 3000 RPM in oil for 48 hours for a secondary drainage capillary pressure curve measurement. From these curves, the relationship between the capillary pressure and corresponding water saturation can be determined very straightforwardly. The primary drainage (circles), imbibition (squares) and secondary drainage (triangles) capillary pressure curves are shown in FIG. 28. The curves of FIG. 28 are physically sensible and closely approximate similar curves described in the literature, for example, Donaldon E. C., Thomas R. D. and Lorenz P. B., SPE Journal, 9(1), 13 (1969). However, the difficulty of conventional measurement methods where a single curve takes 15 times longer than the present method, means that such curves are rarely determined in practice. The present methodology according to embodiments of the present invention allows these curves to be determined much quicker and with relative ease.

The data presented in FIG. 28 provides important information about an oil reservoir.

The primary drainage curve indicated by the circles provides information about the process that takes place when oil displaces water in the rock. The primary drainage capillary pressure curve can also provide information on the pore size.

The imbibition measurement provides the irreducible water saturation value which in FIG. 28 is about 28%. The secondary drainage curve provides a value of residual (irreducible) oil saturation, which in FIG. 28 is about 18% (determined from the difference between 100% saturation and the measured water saturation at the outlet face of about 82%, also shown in FIG. 27. This value indicates that once oil saturation in the rock reaches this level, no more oil can be produced.

The irreducible water saturation indicates how much oil is present in the reserve. A low irreducible water saturation indicates that the oil saturation is high, and vice versa.

The area under the curves indicates how much energy is required to take up a particular fluid, and therefore the wettability of the rock for a particular fluid. In particular, the area under the imbibition (square) curve indicates how much energy is required for water to displace oil and the area under the secondary drainage capillary pressure curve (triangles) indicates how much energy is required for oil to displace water. The area under each curve can be compared, and provides an indication of whether the rock is more wettable by one fluid than another. In the particular example of FIG. 28, the results show that the area under the secondary drainage capillary pressure curve is greater than that of the imbibition capillary pressure curve so that it is easier for water to displace oil than for oil to displace water and therefore the rock is more water wettable than oil wettable.

Modifications and changes to the embodiments described above may be made and will be apparent to those skilled in the art.

The methods and apparatus described herein may be used to measure any other desired parameters in any desired sample and for any application. For example, the methods and apparatus may be used to measure characteristics of any material including the interaction between any porous media and one or more fluids. These materials may include but are not limited to any types of rock, mineral, soil, coal, wood or any form of synthetic material. The fluids used in the methods and apparatus may comprise any gas or liquid.

In any of these methods described herein, any one or more steps may be omitted altogether, as required, or replaced by one or more different method steps, and otherwise modified to suit the particular application.

Embodiments of the method and apparatus may include any one or more features disclosed herein in combination with any one or more other features to the exclusion of any one or more other features disclosed herein.

The invention claimed is:

1. A method of measuring a parameter indicative of fluid content in a porous sample, comprising:
   mounting the porous sample for rotation about an axis such that different portions of the sample are spaced at different distances from the axis;
   rotating the sample about said axis at a substantially constant speed of rotation;
   measuring a first parameter indicative of fluid content in each of said different portions of said sample comprising detecting said fluid by one dimensional magnetic resonance imaging along the sample in the direction of spatial separation between the different portions thereof using a phase encoded magnetic field gradient to spatially resolve each portion along the sample, wherein said magnetic resonance imaging comprises one dimensional single-point ramped imaging, which includes the steps of:
   (a) progressively increasing the gradient of a magnetic field directed in a first direction from zero to a predetermined maximum value;
   (b) applying to the sample an RF pulse at each of a number of different values of magnetic field gradient between zero and said predetermined maximum value;
   (c) detecting a nuclear magnetic resonance (nmr) signal from the sample resulting from each excitation pulse to provide a first set of data comprising respective values of magnetic field gradient and the respective values of the detected nmr signal from the sample;
   (d) after said magnetic field gradient reaches said predetermined maximum in said first direction, reducing said field gradient to zero without applying an RF pulse to said sample;
   (e) progressively increasing the gradient of a magnetic field directed in a second direction opposite to said first direction from zero to a predetermined maximum value;
   (f) applying an RF excitation pulse to the sample at each of a number of different values of magnetic field gradient between zero and said predetermined maximum value;
   (g) detecting a nuclear magnetic resonance signal from said sample resulting from each excitation pulse to provide a second set of data comprising respective values of magnetic field gradient and the respective values of the detected nuclear magnetic resonance signal from the sample;
   (h) determining the values of said first parameter at said different positions along the sample from the first and second sets of data;
   (i) determining the value of a second parameter related to the force to which each portion is subjected due to said rotating of said sample; and
   (j) outputting at least one of:
      (i) the values of the first and second parameters; and
      (ii) data based on said values.

2. A method as claimed in claim 1, wherein said second parameter comprises capillary pressure.

3. A method as claimed in claim 1, wherein the first parameter comprises the amount of said fluid in each of said portions of said sample.

4. A method as claimed in claim 1, comprising measuring the nmr signal at a portion of the sample having a predetermined known level of saturation of said fluid, and determining the value of said parameter indicative of fluid content in each of said different portions of said sample based on the nmr signal at each portion and the measured nmr signal at said portion having a predetermined level of saturation of said fluid.

5. A method as claimed in claim 4, wherein said predetermined known level of saturation of said fluid comprises a 100% saturation level.

6. A method as claimed in claim 1, comprising conditioning the sample with a predetermined known level of saturation of said fluid at each of said different portions thereof, measuring the nmr signal by said one dimensional magnetic resonance imaging at each different portion of the sample when each portion has said predetermined known level of saturation of said fluid, and determining the value of said parameter indicative of fluid content at each said portion of said sample based on the measured nmr signal at each different portion having a predetermined level of saturation and the nmr signal at each portion after rotation of said sample.

7. A method as claimed in claim 6, wherein the predetermined known level of saturation of said fluid at each respective different portion of said sample comprises 100% saturation of said fluid.

8. A method as claimed in claim 1, wherein said sample contains heavy water ($D_2O$) and oil prior to said measuring step, and the fluid detected by said measuring step is oil.

9. A method as claimed in claim 8, further comprising measuring the combined mass of oil and heavy water in the sample, saturating said sample with a fluid, measuring the total volume of fluid in the sample to provide the pore volume of the sample, and determining the volume of oil in the sample based on the pore volume of the sample and the combined mass.

10. A method as claimed in claim 9, further comprising determining the volume normalized oil distribution along the sample based on the detected oil content at each of said different portions thereof and the measured volume of oil in the sample.

11. A method as claimed in claim 10, wherein the step of saturating said sample with fluid comprises saturating said sample with heavy water.

12. A method as claimed in claim 11, further comprising saturating said sample with water, measuring the water content in said different portions of said sample by said one dimensional magnetic resonance imaging, and determining the volume normalized water saturation distribution along the sample based on the measured water content and the volume of the sample.

13. A method as claimed in claim 12; further comprising determining the distribution of heavy water along the sample by subtracting the volume normalized oil distribution from the volume normalized water distribution.

14. A method as claimed in claim 13, further comprising determining the water saturation distribution along the sample after rotation thereof by dividing the volume normalized heavy water distribution after rotation by the volume normalized water distribution when the sample is water saturated.

15. A method as claimed in claim 1, wherein said sample contains a first fluid prior to said measuring step and the method further comprises exposing said sample to a second fluid for introduction into said sample during said rotating step.

16. A method as claimed in claim 15, wherein said first fluid is different from said second fluid.

17. A method as claimed in claim 16, wherein said first and second fluids are such that one fluid can be detected relative to the other fluid, and said first parameter is indicative of the amount of one of said first and second fluids in said portion.

18. A method as claimed in claim 17, further comprising determining a parameter indicative of the amount of the other fluid from the measured parameter indicative of the amount of the one fluid.

19. A method as claimed in claim 18, further comprising determining said parameter from a measurement of the amount of a fluid similar to said other fluid when the sample is saturated by said similar fluid.

20. A method as claimed in claim 18, wherein said one fluid is oil and the other fluid is heavy water $D_2O$.

21. A method as claimed in claim 15, wherein said similar fluid is water ($H_2O$).

22. A method as claimed in claim 1, further comprising introducing first and second fluids into said sample, conditioning the fluid distribution within the sample such that the first fluid has a substantially uniform fluid content in a direction parallel to the radius of rotation of the sample, exposing said conditioned sample to a supply of said second fluid, performing said rotation, and wherein said first parameter is indicative of the content of one of said first and second fluids.

23. A method as claimed in claim 22, further comprising conditioning said first fluid prior to said exposing such that the fluid content is at least one of an irreducible fluid content aid a residual fluid content.

24. A method as claimed in claim 23, wherein said first fluid comprises one of heavy water ($D_2O$) and water ($H_2O$) and said second fluid comprises oil.

25. A method as claimed in claim 24, further comprising performing the steps recited in claim 18 wherein the first fluid is oil and the second fluid is one of heavy water ($D_2O$) and water.

26. A method as claimed in claim 1, wherein the speed of rotation is selected on the basis of a minimum speed to satisfy the condition that the content of fluid in the sample at the inlet face is substantially irreducible.

27. A method as claimed in claim 26, wherein the speed of rotation is selected on the basis of the equation:

$$J = \frac{P_c}{\sigma \cos\theta} \sqrt{\frac{k}{\phi}},$$

where $P_c$ is the capillary pressure, $\theta$ is the contact angle between two fluids, k is the permeability of the sample, $\psi$ is the porosity of the sample and $\sigma$ is the interfacial tension between the two fluids.

28. A method as claimed in claim 27, wherein the speed of rotation is selected by determining a value of rotational speed based on the equation:

$$\omega^2 \geq \frac{2J(S_{wi})\sigma\cos\theta}{\Delta\rho(r_2^2 - r_1^2)\sqrt{k/\phi}}$$

where $J(S_{wi})$ has a value of at least 3, $r_1$ is the distance between the rotational axis and the inlet face of the sample, $r_2$ is the distance between the rotational axis and the outlet face of the sample, $\omega$ is the speed of rotation, $\Delta\rho$ is the difference in density between two fluids, and $\sigma$ is the interfacial tension between the two fluids.

29. A method as claimed in claim 1, further comprising repeating said measuring said first parameter indicative of fluid content in each of said different portions of said sample a time after first performing said measuring said first parameter indicative of fluid content in each of said different portions of said sample.

30. A method as claimed in claim 1, further comprising measuring changes in fluid distribution as a function of time after said totaling the sample about said axis at a substantially constant speed of rotation by repeating said measuring step.

31. A method as claimed in claim 6, comprising determining the ratio of the intensity of the nmr signal measured at each different portion along the sample after rotation of the sample and the intensity of the nmr signal measured at each respective different portion along the sample when said sample is conditioned with said predetermined saturation level of fluid.

32. A method as claimed in claim 1, wherein the element of said fluid detected by said magnetic resonance imaging includes any one of hydrogen, deuterium and fluorine.

33. A method as claimed in claim 1, wherein the magnitude of the free induction decay (FID) signal of said nmr signal is substantially proportional to the amount of fluid in said portion of said sample.

34. A method of measuring a parameter indicative of fluid content in a porous sample, comprising:
measuring a parameter indicative of fluid content in each of a number of different portions of said sample comprising detecting said fluid by one dimensional magnetic resonance imaging along the sample in the direction of spatial separation between the different portions thereof using a phase encoded magnetic field gradient to spatially resolve each portion along the sample, wherein said magnetic resonance imaging comprises one dimensional single-point ramped imaging, which includes the steps of:
(a) progressively increasing the gradient of a magnetic field directed in a first direction from zero to a predetermined maximum value;
(b) applying to the sample an RF pulse at each of a number of different values of magnetic field gradient between zero and said predetermined maximum value;
(c) detecting a nuclear magnetic resonance (nmr) signal from the sample resulting from each excitation pulse to provide a first set of data comprising respective values of magnetic field gradient and the respective values of the detected nmr signal from the sample;
(d) after said magnetic field gradient reaches said predetermined maximum in said first direction, reducing said field gradient to zero without applying an RF pulse to said sample;
(e) progressively increasing the gradient of a magnetic field directed in a second direction opposite to said first direction from zero to a predetermined maximum value;
(f) applying an RF excitation pulse to the sample at each of a number of different values of magnetic field gradient between zero and said predetermined maximum value;
(g) detecting a nuclear magnetic resonance signal from said sample resulting from each excitation pulse to provide a second set of data comprising respective values of magnetic field gradient and the respective values of the detected nuclear magnetic resonance signal from the sample;

(h) determining the values of said parameter at said different positions along the sample from the first and second sets of data; and (i) outputting at least one of:
(i) the values of said parameter; and
(ii) data based on said values.

35. A method as claimed in claim 34, further comprising conditioning the sample with a predetermined known level of saturation of said fluid at each of said different portions thereof prior to measuring said parameter.

36. A method as claimed in claim 34, further comprising repeating said measuring of said parameter indicative of fluid content in each of said different portions of said sample, a time after first performing said measuring.

37. A method as claimed in claim 34, further comprising measuring changes in fluid distribution as a function of time by repeating said measuring step.

38. A method as claimed in claim 34, wherein said sample contains first and second fluids, and said measuring comprises detecting only one of said first and second fluids by said magnetic resonance imaging.

39. A method as claimed in claim 38, wherein the element of said fluid detected by said magnetic resonance imaging includes any one of hydrogen, deuterium and fluorine.

40. A method as claimed in claim 38, wherein said first fluid comprises one of water and heavy water ($D_2O$) and the second fluid comprises oil.

41. An apparatus for measuring a parameter indicative of fluid content in a porous sample comprising a magnetic resonance imaging system which includes a magnet for applying a static magnetic field to said sample, an RF pulse generator for applying RF excitation pulses to said sample, a detector for detecting magnetic induction signals from the sample, a generator for applying a magnetic field gradient to the sample and a controller for controlling the magnetic field gradient, wherein the magnetic resonance imaging system is operable to perform one dimensional single-point ramped imaging, in which said gradient controller is operative to progressively increase the gradient of a magnetic field directed in a first direction from zero to a predetermined maximum value;

the RF pulse generator is operative to apply to the sample an RF pulse at each of a number of different values of magnetic field gradient between zero and said predetermined maximum value;

said detector is operative to detect a nuclear magnetic resonance (nmr) signal from the sample resulting from each excitation pulse to provide a first set of data comprising respective values of magnetic field gradient and the respective values of the detected nmr signal from the sample, the magnetic field gradient controller being operative to reduce the field gradient to zero after said magnetic field gradient reaches said predetermined maximum in said first direction without applying an RF pulse to the sample and progressively increasing the gradient of a magnetic field directed in a second direction opposite to the first direction from zero to a predetermined maximum value;

the RF pulse generator being operative to apply an RF excitation pulse to the sample at each of a number of different values of magnetic field gradient between zero and said predetermined maximum value, said detector being operative to detect a nuclear magnetic resonance signal from the sample resulting from each excitation pulse to provide a second set of data comprising respective values of magnetic field gradient and the respective values of the detected nuclear magnetic resonance signal from the sample, and determining means for determining the values of the parameter indicative of fluid content at said different positions along the sample from the nmr signals in the first and second sets of data.

42. An apparatus as claimed in claim 41, wherein said parameter comprises relative saturation of said fluid in each different portion of said sample and said determining means is operable to determine said relative saturation based on the nmr signal measured by said one dimensional magnetic resonance imaging at each different portion of the sample when each portion has a predetermined known level of saturation of fluid.

43. An apparatus as claimed in claim 41, further comprising a generator for generating the value of a second parameter related to a force to which each portion of said sample is subjected due to rotating said sample about an axis such that different portions of the sample are spaced at different distances from the axis.

44. A method as claimed in claim 43, wherein said second parameter comprises capillary pressure.

45. An apparatus as claimed in claim 41, further comprising a sample holder for rotating the sample about an axis such that different portions of the sample are spaced at different, distances from the axis.

46. An apparatus as claimed in claim 45, wherein said sample holder is adapted to hold said sample such that a portion of said sample extends either side of said axis.

47. An apparatus as claimed in claim 46, wherein said sample holder is adapted to hold a disc shaped sample such that the center of the disc is substantially concentric with said axis.

48. An apparatus as claimed in claim 47, wherein said sample holder is mounted in said magnetic resonance imaging system.

49. An apparatus as claimed in claim 46, wherein said magnetic resonance imaging system is operable to measure fluid distribution along different radii of said sample using spiral single point ramped imaging with $T_1$ enhancement (SPRITE).

50. A method as claimed in claim 1, wherein said sample comprises a porous rock sample.

51. A method as claimed in claim 34, wherein said sample comprises a porous rock sample.

52. An apparatus as claimed in claim 41, wherein said sample comprises a porous rock sample.

* * * * *